US012686719B2

(12) United States Patent
Finkelman et al.

(10) Patent No.: US 12,686,719 B2
(45) Date of Patent: Jul. 21, 2026

(54) SUPPRESSING IgE-MEDIATED ALLERGY BY DESENSITIZATION WITH MONOVALENT ANTI-FCeRIa MONOCLONAL ANTIBODY

(71) Applicants: University of Cincinnati, Cincinnati, OH (US); Children's Hospital Medical Center, Cincinnati, OH (US); Christian-Albrechts-Universitat Zu Kiel, Kiel (DE)

(72) Inventors: Fred Finkelman, Netanya (IL); Suzanne Morris, Mason, OH (US); Marat Khodoun, Mason, OH (US); Crystal Potter, Fairfield, OH (US); Elizabeth Angerman, Fort Thomas, KY (US); Andrew Herr, Cincinnati, OH (US); Matthias Peipp, Hamburg (DE)

(73) Assignees: University of Cincinnati, Cincinnati, OH (US); Children's Hospital Medical Center, Cincinnati, OH (US); Christian-Albrechts-Universitat Zu Kiel, Kiel (DE)

( * ) Notice: Subject to any disclaimer, the term of this patent is extended or adjusted under 35 U.S.C. 154(b) by 988 days.

(21) Appl. No.: 17/277,071

(22) PCT Filed: Sep. 20, 2019

(86) PCT No.: PCT/US2019/052132
§ 371 (c)(1),
(2) Date: Mar. 17, 2021

(87) PCT Pub. No.: WO2020/061441
PCT Pub. Date: Mar. 26, 2020

(65) Prior Publication Data
US 2021/0371519 A1 Dec. 2, 2021

Related U.S. Application Data

(60) Provisional application No. 62/871,964, filed on Jul. 9, 2019, provisional application No. 62/734,676, filed on Sep. 21, 2018.

(51) Int. Cl.
*C07K 16/28* (2006.01)
*A61K 39/00* (2006.01)
*A61P 37/08* (2006.01)
(52) U.S. Cl.
CPC ............ *C07K 16/283* (2013.01); *A61P 37/08* (2018.01); *A61K 2039/505* (2013.01); *A61K 2039/545* (2013.01); *C07K 2317/35* (2013.01); *C07K 2317/52* (2013.01)
(58) Field of Classification Search
CPC .............. C07K 16/283; C07K 2317/35; C07K 2317/52; A61P 37/08; A61K 2039/505; A61K 2039/545
See application file for complete search history.

(56) References Cited

U.S. PATENT DOCUMENTS

| | | | |
|---|---|---|---|
| 5,225,539 A | 7/1993 | Winter | |
| 5,639,641 A | 6/1997 | Pedersen et al. | |
| 8,883,981 B2 * | 11/2014 | Shitara | C07K 16/2887 |
| | | | 530/387.3 |
| 9,868,786 B2 | 1/2018 | Finkelman et al. | |
| 10,086,005 B2 * | 10/2018 | Finkelman | A61K 31/506 |
| 2016/0222115 A1 * | 8/2016 | Huang | C07K 16/2863 |
| 2017/0209573 A1 * | 7/2017 | Bacac | A61K 39/39558 |
| 2018/0092929 A1 * | 4/2018 | Finkelman | A61K 45/06 |
| 2020/0157190 A1 * | 5/2020 | Villanueva | C07K 16/468 |

OTHER PUBLICATIONS

Riske et al. The Journal of Biological Chemistry (1991) 266(17): 11245-11251. (Year: 1991).*
Lloyd et al. Protein Engineering, Design and Selection (2009) 22(3): 159-168. (Year: 2009).*
Schroeder and Cavacini. Journal of Allergy and Clinical Immunology (2010) 125(2, Suppl.2): S41-S52. (Year: 2010).*
Sela-Culang et al. Frontiers in Immunology (2013) 4: 302. (Year: 2013).*
Hong et al. Yonsei Medical Journal (2016) 57(6): 1412-1419. (Year: 2016).*
Gunasekaran (The Journal of Biological Chemistry (2010) 285(25): 19637-19646 (Year: 2010).*
EP Communication pursuant to Article 94(3) EPC dated Nov. 23, 2023 pertaining to EP application No. 19863325.7 filed Mar. 16, 2021, pp. 1-5.
Ganglberger, E. et al. "Monovalent fusion proteins of immuno-globulin E mimotopes are safe for therapy of type I allergy" The FASEB Journal, Sep. 17, 2001, pp. 1-16, 10.1096/fj.00-0888fje.
International Search Report & Written Opinion dated Jan. 24, 2020 pertaining to PCT International application No. PCT/US2019/052132 filed Sep. 20, 2019, pp. 1-20.
Yu, X. et al. "Monovalent Fc receptor blockade by an anti-Fcγ receptor/albumin fusion protein ameliorates murine ITP with abrogated toxicity" Blood, Jan. 7, 2016, pp. 132-138, vol. 127, No. 1.
Verhoeyen et al., 1988, Science, 239: 1534-1536 (Reshaping human antibodies: grafting an antilysozyme activity.
Riechmann et al., 1988, Nature, 332:323-327.
Jones et al., 1986, Nature, 321 :522-525.

(Continued)

*Primary Examiner* — Brad Duffy
*Assistant Examiner* — Elizabeth A Shupe
(74) *Attorney, Agent, or Firm* — Dinsmore & Shohl LLP

(57) ABSTRACT

A monovalent monoclonal antibody is provided, the antibody including one light chain, one heavy chain, and one truncated heavy chain, wherein the truncated heavy chain lacks a variable domain and a CH1 domain and wherein the antibody specifically binds an epitope of FcεRIα. Also provided are methods of desensitizing a subject to an allergen, methods of treating an allergy, and methods of preventing an allergic reaction in a subject having an allergy.

13 Claims, 20 Drawing Sheets

Specification includes a Sequence Listing.

(56)                    References Cited

OTHER PUBLICATIONS

Lefranc, M.P. et al., Dev. Comp. Immunol. 27: 55-77 (2003).
Chothia and Lesk, J Mol. Biol. 196:901-917 (1987).
Al-Iazikani et al., J. Malec. Biol. 273:927-948 (1997).

* cited by examiner

SUPPRESSING IgE-MEDIATED ALLERGY BY DESENSITIZATION WITH MONOVALENT ANTI-FCeRIa MONOCLONAL ANTIBODY

CROSS-REFERENCE TO RELATED APPLICATIONS

The present application claims is a §371 National Stage entry of International Application No. PCT/US2019/052132, filed Sep. 20, 2019, which claims priority to U.S. Provisional Application Ser. No. 62/734,676, flied Sep. 21, 2018, and U.S. Provisional Application Ser. No. 62/871,964, filed Jul. 9, 2019, each of which is incorporated herein by reference in its entirety.

STATEMENT REGARDING FEDERALLY SPONSORED RESEARCH OR DEVELOPMENT

This invention was made with government support under 1R01AI113162 awarded by the National Institutes of Health. The government has certain rights in the invention.

SEQUENCE LISTING

Applicant hereby incorporates by reference a CRF sequence listing submitted herewith having a file name Sequence Listing 10738 748.txt, created on Sep. 9, 2019.

The nucleic and amino acid sequences listed in the accompanying sequence listing are shown using standard abbreviations as defined in 37 C.F.R. 1.822. Only one strand of each nucleic acid sequence is shown, but the complementary strand is understood as included by any reference to the displayed strand. In the accompanying sequence listing:

SEQ ID NO: 1 represents a nucleic acid sequence encoding a light chain variable region of a monovalent (mv) anti-huFcεRIα monoclonal antibody (mAb);

SEQ ID NO: 2 represents a nucleic acid sequence encoding a heavy chain variable region of mv anti-huFcεRIα mAb;

SEQ ID NO: 3 represents a light chain variable region of mv anti-huFcεRIα mAb;

SEQ ID NO: 4 represents a heavy chain variable region of mv anti-huFcεRIα mAb;

SEQ ID NO: 5 represents a light chain complementarity-determining region (CDR) 1 of mv anti-huFcεRIα mAb;

SEQ ID NO: 5 represents a light chain complementarity-determining region (CDR) 1 of mv anti-huFcεRIα mAb;

SEQ ID NO: 6 represents a light chain CDR2 of mv anti-huFcεRIα mAb;

SEQ ID NO: 7 represents a light chain CDR3 of mv anti-huFcεRIα mAb;

SEQ ID NO: 8 represents a heavy chain CDR1 of mv anti-huFcεRIα mAb;

SEQ ID NO: 9 represents a heavy chain CDR2 of mv anti-huFcεRIα mAb;

SEQ ID NO: 10 represents a heavy chain CDR3 of mv anti-huFcεRIα mAb;

SEQ ID NO: 11 represents a full IE7 mAb light chain;

SEQ ID NO: 12 represents a full IE7 mAb heavy chain; and

SEQ ID NO: 13 represents a truncated heavy chain derived from the heavy chain of IE7 mAb, including a leader sequence that is cleaved during secretion.

BACKGROUND

Allergic disorders, including allergic rhinitis, asthma, atopic dermatitis, food allergy and anaphylaxis are an increasingly common cause of morbidity in developed countries. Anaphylaxis, in particular, is a life-threatening illness with an estimated lifetime prevalence of 1-2% in the United States. All of these allergic disorders are mediated, to some extent, by antigen activation of mast cells and basophils by the crosslinking of antigen-specific IgE bound to the alpha (α) chain of the high affinity IgE receptor, FcεRI. IgE/mast cell/basophil-mediated allergy and anaphylaxis can be severe and rapid in onset and can occur after multiple exposures or the initial exposure to an allergen. Foods, drugs, and insect venoms are common causes of IgE-mediated anaphylaxis. IgE-mediated allergy to these substances can have severe adverse effects on quality of life and on ability to treat disease and can be lethal.

Immunotherapeutic approaches for treatment of IgE-mediated allergy have been explored. Omalizumab is an anti-IgE monoclonal antibody that binds only to IgE that is not FcεR-associated; however, it is slow-acting and works poorly in patients with high IgE levels. An alternative approach is the use of monoclonal antibodies that target FcεRIα; however, there have been safety concerns with this approach.

Rapid desensitization (RD) is a process by which individuals who have IgE-mediated allergy to a specific antigen are made temporarily unresponsive to that antigen by exposing them to the antigen. RD was used to treat penicillin allergy as early as 1946. Drug RD is initiated by infusing the allergenic drug at a dose too small to induce a clinical reaction, then increasing it every 15-60 minutes until a full therapeutic dose is tolerated. Although RD with allergens can decrease the risk of subsequent anaphylaxis, this procedure is not without risk. It frequently has adverse effects, including systemic anaphylaxis, typically works for only a short time if not maintained by daily allergen exposure, and is allergen-specific.

A need persists for a safe, efficacious, convenient way to rapidly suppress IgE/basophil/mast cell-mediated disease without the drawbacks of antigen RD.

SUMMARY

Some of the embodiments of the present disclosure are summarized below. Additional embodiments are described in the Detailed Description, Examples, Figures, and Claims sections of this disclosure. The description in each section of this disclosure is intended to be read in conjunction with the other sections. Furthermore, the various embodiments described in each section of this disclosure can be combined in various different ways, and all such combinations are intended to fall within the scope of the present invention.

While strong FcεRI crosslinking induces the mast cell/basophil activation and degranulation that causes allergic signs and symptoms, persistent, low-level crosslinking of FcεRI removes IgE from these cells and desensitizes them without inducing sufficient degranulation to cause allergy manifestations. The present disclosure shows that IgE-mediated allergy can safely be suppressed by a single administration of a recombinant monovalent Fab/Fc derivative anti-FcεRIα antibody, which persistently crosslinks FcεRI to a limited extent.

In one embodiment, a monovalent anti-huFcεRIα monoclonal antibody (mAb) is provided, comprising one light chain, one heavy chain, and one truncated heavy chain, wherein the truncated heavy chain lacks a variable domain and a CH1 domain, wherein the mAb specifically binds an epitope of FcεRIα. In some embodiments, the mAb does not compete with IgE for binding to FcεRIα. In some embodiments, the mAb binds to human FcεRIα.

In certain embodiments, the light chain is a kappa chain. The light chain can comprise a variable region encoded by SEQ ID NO: 1. The light chain can comprise a variable region having SEQ ID NO: 3. The light chain can comprise complementarity-determining region (CDR) 1 having the sequence QDINNY (SEQ ID NO: 5), CDR2 having the sequence RAN (SEQ ID NO: 6), and CDR3 having the sequence LLYNEFPWM (SEQ ID NO: 7).

In certain embodiments, the heavy chain is a gamma chain. In one embodiment, the heavy chain is a gamma subclass 4 heavy chain (IgG4). The heavy chain constant region may be human. The heavy chain can comprise a variable region encoded by SEQ ID NO: 2. The heavy chain can comprise a variable region having SEQ ID NO: 4. The heavy chain can comprise CDR1 having the sequence GFTFSFYG (SEQ ID NO: 8), CDR2 having the sequence ISGGGNYT (SEQ ID NO: 9), and CDR3 having the sequence VRAYYGNWNSY (SEQ ID NO: 10). One or both of the heavy chain and the truncated heavy chain can comprise one or more mutations in the constant region to promote dimerization of the heavy chain and the truncated heavy chain. In one embodiment, the heavy chain comprises a E356K mutation and/or a D399K mutation. In one embodiment, the truncated heavy chain comprises a K392D mutation and/or a K409D mutation. In some embodiments, the monovalent anti-huFcεRIα mAb is a chimeric antibody, in which the constant region of the heavy chain is from human IgG1 (γ1) and the constant region of the light chain is from human kappa chain.

Also provided is a pharmaceutical composition comprising the anti-FcεRIα monovalent mAb. In certain embodiments, the pharmaceutical composition is for use in treating an allergy or desensitizing a subject to an allergen. Also provided is the use of the anti-FcεRIα monovalent mAb in the manufacture of a medicament for the treatment of an allergy.

In another embodiment, a polynucleotide or combination of polynucleotides encoding the anti-FcεRIα monovalent mAb is provided. A vector and a host cell comprising the polynucleotide or combination of polynucleotides are also provided.

In another embodiment, provided are methods of desensitizing a subject to allergen, methods of treating an allergy, and methods of preventing an allergic reaction in a subject having an allergy. In some embodiments, the allergic reaction is anaphylaxis. The allergen can be, for example, selected from the group consisting of protein, polysaccharide, lipid, polynucleotide, food, pollen, mold spores, dust, animal dander, insect debris, blood serum, drugs, cosmetics, and combinations thereof. In certain embodiments, the allergen is a food allergen selected from the group consisting of eggs, milk, peanuts, tree nuts, soy, sesame, crustacean shellfish, and wheat.

In one embodiment, a method comprises administering to a subject with an allergy a plurality of doses of a first anti-FcεRIα mAb, wherein the doses are administered over a period of 1 to 4 days, and wherein each dose is lower than a level required to induce shock. In some embodiments, a dose of the first anti-FcεRIα mAb is administered every 1-4 hours. In some embodiments, each dose is the same as or higher than, for example double or triple, each immediately preceding dose. In certain embodiments, the method further comprises administering a plurality of doses of a second anti-FcεRIα mAb, wherein each dose is lower than a level required to induce shock. The second anti-FcεRIα mAb can be co-administered with the first anti-FcεRIα mAb, wherein the total dose of anti-FcεRIα mAb is lower than a level required to induce shock. The total dose of anti-FcεRIα mAb is the dose of the first anti-FcεRIα mAb plus the dose of the second anti-FcεRIα mAb. In some embodiments, each total dose of anti-FcεRIα mAb is the same as or higher than, for example double or triple, each immediately preceding total dose.

A variety of anti-FcεRIα mAbs can be used in the methods of desensitizing a subject to allergen, methods of treating an allergy, and methods of preventing an allergic reaction in a subject having an allergy. In some embodiments, the anti-FcεRIα mAb is a monovalent mAb. In some embodiments, the anti-FcεRIα mAb is IE7 or IB10. In methods comprising a first anti-FcεRIα mAb and a second anti-FcεRIα mAb, the first and second antibodies can each bind to a different epitope of FcεRIα. In one aspect, the first anti-FcεRIα mAb is IE7 and the second anti-FcεRIα mAb is D310.

Another method comprises administering to a subject with an allergy a first dose of a first anti-FcεRIα mAb at a dose that is lower than a level required to induce shock, wherein the first anti-FcεRIα mAb is a monovalent anti-huFcεRIα mAb comprising one light chain, one heavy chain, and one truncated heavy chain, wherein the truncated heavy chain lacks a variable domain and a CH1 domain, wherein the mAb specifically binds an epitope of FcεRIα, optionally the epitope that is bound by the mAb IE7. In some embodiments, the mAb does not compete with IgE for binding to FcεRIα. In some embodiments, the mAb binds to human FcεRIα.

In a particular embodiment, the method further comprises subsequently administering a second dose of the first anti-FcεRIα mAb at a dose that is lower than a level required to induce shock. The method can further comprise administering additional doses of the first anti-FcεRIα mAb every 1-4 weeks or every 1-6 months, wherein each additional dose is lower than a level required to induce shock.

In another embodiment, the method further comprises subsequently administering a first dose of a second anti-FcεRIα mAb at a dose that is lower than a level required to induce shock. The method can further comprise co-administering a second dose of the first anti-FcεRIα mAb with the first dose of the second anti-FcεRIα mAb, wherein the total dose of anti-FcεRIα mAb is lower than a level required to induce shock.

In certain embodiments, the first dose of the second anti-FcεRIα mAb is administered about 24 hours after the first dose of the first anti-FcεRIα mAb. Additional doses of the second anti-FcεRIα mAb or additional doses of the first anti-FcεRIα mAb and the second anti-FcεRIα mAb can be administered, for example, every 1-4 weeks, wherein each additional dose or total dose is lower than a level required to induce shock. These and other objects, features, embodiments, and advantages will become apparent to those of ordinary skill in the art from a reading of the following detailed description and the appended claims.

BRIEF DESCRIPTION OF THE FIGURES

FIG. 21 shows that mv huIgG1 IE7-induced anaphylaxis and desensitization are blocked by anti-FcγR mAb.

FIG. 22 shows that decreasing mv IE7 avidity for FcγRs by replacing huIgG1 with huIgG4 heavy chain constant regions prevents direct induction of anaphylaxis in IL-4C/propranolol-treated huFcεRIα/IL-4Rα$^{F709}$ mice and reduces protection against IgE-mediated anaphylaxis.

DETAILED DESCRIPTION

Figure 1:
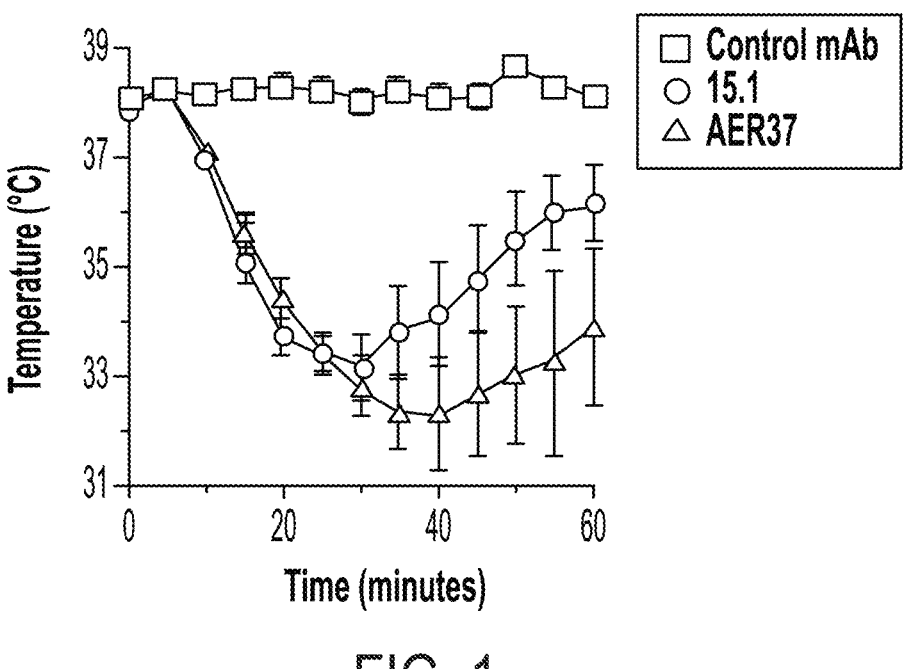
FIG. 1 shows that anti-human (hu) FcεRIα mAbs induce anaphylaxis in huFcεRIα mice (BALB/c genetic background mice that lack a functional gene for mouse FcεRIα and express a transgene that encodes huFcεRIα). These mice express functional, chimeric FcεRIα on mast cells and basophils that is composed of huFcεRIα chain and mouse FcεRI β and γ chains. HuFcεRIα mice (4/group) were injected i.v. with 100 μg of 15.1 anti-huFcεRIα mAb, AER-37 anti-huFcεRIα mAb or an isotype control mAb and followed for changes in rectal temperature for the next 60 min. Means and SEMs are shown in this and subsequent figures. Additional studies showed that as little as 3 μg of 15.1 or AER-37 is sufficient to induce considerable hypothermia in naïve huFcεRIα mice.

Described herein are monovalent (mv) mAbs to FcεRIα. In particular, the present disclosure describes recombinant mv Fab/Fc derivatives of anti-huFcεRIα mAbs that bind FcεRI, regardless of its association with IgE. As a result of their single Fab and complete Fc, these mAbs do not directly crosslink FcεRI, but induce persistent, low-level FcεRI crosslinking. The mv mAbs of the present disclosure achieve safe and effective allergen-independent desensitization with a single administration. Also disclosed herein are methods of allergen desensitization, allergy treatment, and prevention of allergic reactions using an extended desensitization protocol and protocols using the mv mAbs of the disclosure with or without subsequent injections of a divalent (dv) form of the same antibodies.

These mv mAbs were tested in three different types of transgenic mice: (a) huFcεRIα mice, which have human (rather than mouse) FcεRIα; (b) huFcεRIα/IL-4Rα$^{F709}$ mice, which have human FcεRIα, as well as an IL-4Rα$^{F709}$ mutation that enhances the pro-allergic effects of IL-4 and IL-13; and (c) reNRGS mice, which are immunodeficient, hu IL-3-, GM-CSF- and SCF-producing mice that have developed large numbers of activated human mast cells following reconstitution with human cord blood cells. In some experiments, mice were pre-treated with a long-acting form of IL-4 (IL-4C) or IL-4C and the β-adrenergic receptor antagonist propranolol to increase their sensitivity to histamine and other mediators by a factor of approximately fifty.

This disclosure demonstrates: (1) that humanized mice can be safely protected against IgE-mediated anaphylaxis and food allergy by rapid desensitization with anti-huFcεRIα mAb or by a single injection of the mv Fab/Fc of this mAb; (2) that desensitization is characterized by decreased mast cell responsiveness to FcεRI crosslinking, loss of most IgE, and some loss of FcεRI; (3) that rapid desensitization with anti-FcεRIα mAb is safer and lasts longer than rapid desensitization with a relevant allergen; (4) that the greater the sensitivity of mice to FcεRI crosslinking, the longer it takes to safely and rapidly desensitize them; (5) that desensitization can be maintained by repeated injections of anti-FcεRIα mAb; (6) that FcεRI crosslinking by mv anti-FcεRIα mAbs is mediated by the simultaneous binding of these mAbs to mast cell/basophil FcεRI and to FcγRs; (7) the greater safety of mv over dv anti-FcεRIα mAbs for single dose desensitization of mast cells and suppression of IgE-mediated allergy; (8) the importance of deaggregating mv anti-FcεRIα mAbs that will be used for desensitization; (9) the contribution of avidity for FcγRs to induction of anaphylaxis and suppression of IgE-mediated disease by mv anti-FcεRIα mAbs; (10) the ability to decrease induction of anaphylaxis by a mv form of the anti-huFcεRIα mAb, IE7, by producing a variant that has huIgG4, rather than huIgG1 heavy chain constant regions, consistent with the lower avidity of huIgG4 than huIgG1 for FcγRs; (11) that suppression of IgE-mediated anaphylaxis is not entirely due to removal of IgE from mast cells; and (12) that desensitization by mv IE7 is accompanied by selective loss of some mast cell signaling molecules: SYK, phospho-SYK, and phospho-SHIP, but neither phospho-AKT nor phospho-ERK.

Definitions

Unless defined otherwise, all technical and scientific terms used herein have the same meaning as commonly understood by one of ordinary skill in the art to which this subject matter is related.

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Units, prefixes, and symbols are denoted in their Systeme International de Unites (SI) accepted form. Numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10. Where a numeric term is preceded by "about," the term includes the stated number and values ±10% of the stated number. The headings provided herein are not limitations of the various aspects or embodiments of the disclosure, which can be had by reference to the specification as a whole. Accordingly, the terms defined immediately below are more fully defined by reference to the specification in its entirety.

Amino acids are referred to herein by their commonly known three-letter symbols or by the one-letter symbols recommended by the IUPAC-IUB Biochemical Nomenclature Commission. Nucleotides, likewise, are referred to by their commonly accepted single-letter codes. Unless otherwise indicated, amino acid sequences are written left to right in amino to carboxy orientation, and nucleic acid sequences are written left to right in 5' to 3' orientation.

Wherever embodiments are described with the language "comprising," otherwise analogous embodiments described in terms of "consisting of" and/or "consisting essentially of" are included.

"FcεRI" refers to the high-affinity receptor for the Fc region of the epsilon heavy chain of immunoglobulin E (IgE). FcεRT is constitutively expressed on mast cells and basophils, and can be induced in eosinophils. FcεRI is comprised of an alpha chain, a beta chain, and two gamma chains. The IgE binding site of FcεRI is on the alpha chain. An "anti-FcεRIα antibody" binds specifically to the alpha chain of FcεRT. Some anti-FcεRIα antibodies compete with IgE for binding to FcεRIα. Other anti-FcεRIα antibodies do not compete with IgE for binding to FcεRIα.

The term "antibody" refers to an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. The terms "antibody" or "immunoglobulin" are used interchangeably herein.

A typical IgG antibody comprises at least two γ heavy (H) chains and two light (L) chains interconnected by disulfide bonds. Each γ chain is comprised of a heavy chain variable region (VH) and a γ heavy chain constant region. The γ heavy chain constant region is comprised of three domains, CH1, CH2, and CH3. Each light chain is comprised of a light chain variable region (VL) and a light chain constant region (CL). The light chain constant region is comprised of one domain, Cl. The variable regions of the heavy and light chains contain a binding domain that interacts with an antigen. The constant regions of the antibodies can mediate the binding of the immunoglobulin to host tissues or factors, including various cells of the immune system (e.g. effector cells) and the first component (Clq) of the classical complement system.

For purposes of the present disclosure, a "monovalent" molecule contains a single antigen-binding region. A "bivalent" or "divalent" molecule contains two antigen-binding regions, which each may bind the same or different antigen molecules. When each of the antigen binding regions of a bivalent molecule binds the same antigen, it is "mono-specific." When each of the antigen-binding regions of a bivalent molecule binds a different antigen or a different epitope on the same antigen, it is "bi-specific." For example, native antibodies are bivalent mono-specific molecules. The terms "bivalent," "divalent," and the abbreviation "dv" are used herein interchangeably.

Antibodies can be of any the five major classes (isotypes) of immunoglobulins: IgA, IgD, IgE, IgG and IgM, or subclasses thereof (e.g. IgG1, IgG2, IgG3, IgG4, IgA1 and IgA2), based on the identity of their heavy-chain constant domains referred to as alpha, delta, epsilon, gamma, and mu respectively. Mutated subclasses of immunoglobulins, for example, IgG2σ, are also included in the scope of the disclosure. The different classes of immunoglobulins have different and well-known subunit structures and three-dimensional configurations. There are two classes of mammalian light chains, lambda and kappa.

The VH and VL regions can be further subdivided into regions of hypervariability, termed complementarity-determining regions (CDRs), interspersed with regions that are more conserved, termed framework (FW) regions. The CDRs in each chain are held together in close proximity by the FW regions and, with the CDRs from the other chain, contribute to the formation of the antigen-binding site of antibodies. Each VH and VL is composed of three CDRs and four FWs, arranged from amino-terminus to carboxy-terminus in the following order: FW1, CDR1, FW2, CDR2, FW3, CDR3, FW4.

There are at least two techniques for determining CDRs: (1) an approach based on cross-species sequence variability (Kabat et al., *Sequences of Proteins of Immunological Interest,* 5th Ed. Public Health Service, National Institutes of Health, Bethesda, Md. (1991)); and (2) an approach based on crystallographic studies of antigen-antibody complexes (Al-lazikani et al., *J. Molec. Biol.* 273:927-948 (1997)). In addition, combinations of these two approaches are sometimes used in the art to determine CDRs.

The amino acid position numbering as in Kabat, refers to the numbering system used for heavy chain variable domains or light chain variable domains (approximately residues 1-107 of the light chain and residues 1-113 of the heavy chain). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52σ, according to Kabat) after residue 52 of H2 and inserted residues (e.g., residues 82σ, 82b, and 82c, etc., according to Kabat) after heavy chain FW residue 82.

TABLE 1

| Loop | Kabat | AbM | Chothia |
|------|-------|-----|---------|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B (Kabat Numbering) | H26-H32 . . . 34 |
| H1 | H31-H35 | H26-H35 (Chothia Numbering) | H26-H32 |
| H2 | H50-H65 | H50-H58 | H52-H56 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. See Table 1.

IMGT (ImMunoGeneTics) also provides a numbering system for the immunoglobulin variable regions, including the CDRs. See, e.g., Lefranc, M. P. et al., *Dev. Comp. Immunol.* 27: 55-77 (2003). The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97. As used throughout the specification, the CDR sequences described correspond to the IMGT numbering system.

A "monoclonal antibody" (mAb) refers to a homogeneous antibody population that is involved in the highly specific recognition and binding of a single antigenic determinant, or epitope. This is in contrast to polyclonal antibodies, which typically include different antibodies directed against different antigenic determinants. The term "monoclonal" can apply to both intact and full-length monoclonal antibodies, as well as to antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., 1986, *Nature*, 321:522-525; Riechmann et al., 1988, *Nature*, 332:323-327; Verhoeyen et al., 1988, *Science*, 239:1534-1536). In some instances, the Fv framework region (FW) residues of a human immunoglobulin are replaced with the corresponding residues in an antibody from a non-human species that has the desired specificity, affinity, and capability.

Humanized antibodies can be further modified by the substitution of additional residues either in the Fv framework region and/or within the replaced non-human residues to refine and optimize antibody specificity, affinity, and/or capability. In general, humanized antibodies will comprise substantially all of at least one, and typically two or three, variable domains containing all or substantially all of the CDR regions that correspond to the non-human immunoglobulin whereas all or substantially all of the FR regions are those of a human immunoglobulin consensus sequence. Humanized antibody can also comprise at least a portion of an immunoglobulin constant region or domain (Fc), typically that of a human immunoglobulin. Examples of methods used to generate humanized antibodies are described in U.S. Pat. Nos. 5,225,539 and 5,639,641.

The term "human antibody" means an antibody produced by a human or an antibody having an amino acid sequence corresponding to an antibody produced by a human made using any technique known in the art. The definition of a human antibody includes intact or full-length antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

The term "antigen-binding fragment" refers to a portion of an intact antibody comprising the complementarity determining variable regions of the antibody. Fragments of a full-length antibody can be an antigen-binding fragment of an antibody. Examples of antibody fragments include, but are not limited to Fab, Fab', F(ab')2, and Fv fragments, linear antibodies, single chain antibodies (e.g., ScFvs), and multispecific antibodies formed from antibody fragments.

An "isolated" molecule is one that is in a form not found in nature, including those which have been purified.

A "polynucleotide," as used herein can include one or more "nucleic acids," "nucleic acid molecules," or "nucleic acid sequences," and refers to a polymer of nucleotides of any length, and includes DNA and RNA. The polynucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

The term "vector" means a construct, which is capable of delivering and, in some embodiments expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "inhibit," "block," and "suppress" are used interchangeably and refer to any statistically significant decrease in occurrence or activity, including full blocking of the occurrence or activity. For example, "inhibition" can refer to a decrease of about 10%, 20%, 30%, 40%, 50%, 60%, 70%, 80%, 90% or 100% in activity or occurrence. An "inhibitor" is a molecule, factor, or substance that produces a statistically significant decrease in the occurrence or activity of a process, pathway, or molecule.

An "active agent" is an ingredient that is intended to furnish pharmacological activity or other direct effect in the diagnosis, cure, mitigation, treatment, or prevention of disease, or to affect the structure or any function of a subject's body. The active agent can be in association with one or more other ingredients, and can be, but is not necessarily, in a finished dosage form.

An "effective amount" of an active agent is an amount sufficient to carry out a specifically stated purpose. In embodiments, an effective amount of an active agent is an amount that is sufficient to desensitize a subject to an allergen without inducing anaphylactic shock.

The term "pharmaceutical composition" refers to a preparation that is in such form as to permit the biological activity of the active ingredient to be effective and which contains no additional components that are unacceptably toxic to a subject to which the composition would be administered. Such composition can be sterile and can comprise a pharmaceutically acceptable carrier, such as physiological saline. Suitable pharmaceutical compositions can comprise one or more of a buffer (e.g. acetate, phosphate, or citrate buffer), a surfactant (e.g. polysorbate), a stabilizing agent (e.g. human albumin, polyol, or amino acid), a preservative (e.g. benzyl alcohol or sodium benzoate), an absorption promoter to enhance bioavailability and/or other conventional solubilizing or dispersing agents. Choice of excipients depends upon dosage form, the active agent to be delivered, and the disease or disorder to be treated or prevented.

"Equal doses" are two or more doses of an active agent, wherein each subsequent dose is the same as, or equal to, the first dose of the active agent. Each dose administered in the methods of the present disclosure is lower than a level required to induce shock in the subject to whom the dose is administered.

"Sequentially escalating doses" are two or more doses of an active agent, wherein the second dose is greater than the first, the third is greater than the second, and so forth, such that the subsequent dose is greater than the immediately preceding dose. Each subsequent dose can be larger by a determined amount or can be characterized in relation to the first dose or the immediately preceding dose, such as each subsequent dose is doubled or tripled in relation to the first dose or in relation to the immediately preceding dose.

"Shock" in a subject is a clinical diagnosis that is typically characterized by change in the subject's temperature, changes in circulatory function, pallor, sweating, weak pulse, and/or very low blood pressure.

An "allergen" is a substance that produces an immune response; such responses can include hypersensitivities and allergies. The allergen can, for example, be a protein, can be from food or can be from the environmental surroundings.

Allergens may be naturally occurring or of synthetic origin and include, among other things, pollen, mold spores, dust, animal dander, insect debris, foods, blood serum, drugs, and cosmetics. Common food allergens include eggs, milk, peanuts, tree nuts, soy, sesame, crustacean shellfish, and wheat.

A "subject" or "individual" or "animal" or "patient" or "mammal," is any subject, particularly a mammalian subject, for whom diagnosis, prognosis, or therapy is desired. Mammalian subjects include humans, domestic animals, farm animals, sports animals, and laboratory animals including, e.g., humans, non-human primates, canines, felines, porcines, bovines, equines, rats, mice, rabbits, and the like.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already suffering from the disorder. In certain embodiments, a subject is successfully "treated" for a disease or disorder according to the methods provided herein if the patient shows, e.g., total, partial, or transient alleviation or elimination of symptoms associated with the condition, disease, or disorder; diminishment of the extent of the condition, disease, or disorder; stabilization (i.e., not worsening) of the condition, disease, or disorder; delay in onset or slowing of progression of the condition, disease or disorder; amelioration of the condition, disease, or disorder, including partial or total remission; and/or prolonged survival, as compared to expected survival if not receiving treatment. In the context of the present disclosure, "desensitization" to an allergen is synonymous with treating an allergic disorder and with preventing or reducing an allergic reaction to an allergen. One example of treatment is reduction or amelioration of symptoms associated with an allergic reaction, such as anaphylaxis, allergic rhinitis, asthma, atopic dermatitis, hives, and/or itching.

Monoclonal Antibodies

The methods, uses, and compositions described herein comprise anti-FcεRIα mAbs. Examples of suitable mAbs include, for example, AER-37 (CRA-1), 15.1, IE7, and D310.

In a specific embodiment, the anti-FcεRIα mAb is IE7. A biological material deposit of the IE7 hybridoma was made on Jun. 29, 2018 under the terms of the Budapest Treaty as ATCC® Patent Deposit Designation PTA-125115 with the American Type Culture Collection (ATCC®), P.O. Box 1549, Manassas, Va., 20108, USA.

```
IE7 comprises a light chain variable region
encoded by SEQ ID NO: 1:
gatatcgtga tgacccaaac tccatcttcc atgtatgcat ctctaggaga gagagtcact atcacttgca aggcgagtca ggacattaat aactatttaa gctggttcca gcagaaacca gggagatctc ctaagaccct gatctatcgt gcaaacagat tgatggatgg ggtcccatca aggatcagag gcagtggatc tgggcaagat tattctctca ccatcagcag cctggagtat gaagatatgg gaatttatta ttgtctacta tataatgagt ttccgtggat gttcggtgga ggcaccaagc tggaaatcaa acgg.
```

-continued

IE7 comprises a light chain variable region
having SEQ ID NO: 3:
DIVMTQTPSSMYASLGERVTITCKAS<u>*QDINNY*</u>LSWFQQKPGRSPKTLIY <u>*RAN*</u>RLMDGVPSRIRGSGSGQDYSLTISSLEYEDMGIYYC<u>*LLYNEFPWM*</u>F GGGTKLEIKR,
wherein the CDRs are indicated by underlined,
italicized, bold type.

The full IE7 light chain has SEQ ID NO: 11:
MYRMQLLSCIALSLALVTNSDIVMTQTPSSMYASLGERVTITCKASQDI

NNYLSWFQQKPGRSPKTLIYRANRLMDGVPSRIRGSGSGQDYSLTISSL

EYEDMGIYYCLLYNEFPWMFGGGTKLEIKRTVAAPSVFIFPPSDEQLKS

GTASVVCLLNNFYPREAKVQWKVDNALQSGNSQESVTEQDSKDSTYSLS

STLTLSKADYEKHKVYACEVTHQGLSSPVTKSFNRGEC.

IE7 comprises a heavy chain variable region
encoded by SEQ ID NO: 2:
caggtgcagc tgcaggagtc aggggggagac gtagtgaagc ctggagggtc cctgaaactc tcctgtgcag cctctggatt cactttcagt ttctatggca tgtcttgggt tcgtcagact ccagacaaga aactggagtg ggtcgcaacc attagtggtg gtggtaatta cacctactat ccagacagtg tgaaggggcg attcaccatc tccagagaca atgccatgaa cacccttttac ctgcaaatga acagtctgaa gtctgaagac acagccatgt attattgtgt gagagcctac tatggtaatt ggaattctta ctggggccaa gggactctgg tcactgtctc t.

IE7 comprises a heavy chain variable region
having SEQ ID NO: 4:
QVQLQESGGDVVKPGGSLKLSCAAS<u>*GFTFSFYG*</u>NISWVRQTPDKKLEWV AT<u>*ISGGGNYT*</u>YYPDSVKGRFTISRDNAMNTLYLQMNSLKSEDTAMYYC <u>*VRAYYGNWNSY*</u>WGQGTLVTVS,
wherein the CDRs are indicated by underlined,
italicized, bold type.

The full IE7 heavy chain has SEQ ID NO: 12:
MYRMQLLSCIALSLALVTNSISQVQLQESGGDVVKPGGSLKLSCAASGF

TFSFYGMSWVRQTPDKKLEWVATISGGGNYTYYPDSVKGRFTISRDNAM

NTLYLQMNSLKSEDTAMYYCVRAYYGNWNSYWGQGTLVTVSASTKGPSV

FPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQ

GNVFSCSVMHEALHNHYTQKSLSLSPGK.

In another embodiment, the anti-FcεRIα mAb is IB10. A biological material deposit of the IB10 hybridoma was made on Jun. 29, 2018 under the terms of the Budapest Treaty as ATCC® Patent Deposit Designation PTA-125116 with the American Type Culture Collection (ATCC®), P.O. Box 1549, Manassas, Va., 20108, USA.

In embodiments, the anti-FcεRIα mAb is a monovalent mAb comprising one light chain, one heavy chain, and one truncated heavy chain, wherein the truncated heavy chain lacks a variable domain and a CH1 domain.

In some embodiments, the mv mAb is derived from IE7.

In certain embodiments, the light chain is a kappa light chain and comprises a light chain variable region encoded by SED ID NO: 1 or SEQ ID NO: 3. In embodiments, the mv mAb comprises complementarity-determining region (CDR) 1 having the sequence QDINNY (SEQ ID NO: 5), CDR2 having the sequence RAN (SEQ ID NO: 6), and CDR3 having the sequence LLYNEFPWM (SEQ ID NO: 7) of IE7. In embodiments, the mv mAB comprises the light chain of IE7 (SEQ ID NO: 11).

In certain embodiments, the heavy chain is a gamma chain. In embodiments, the heavy chain is a gamma subclass 4 heavy chain (IgG4). The heavy chain constant region is preferably human. In one embodiment, the heavy chain comprises a variable region encoded by SEQ ID NO: 2. In another embodiment, the heavy chain comprises a variable region of IE7 having SEQ ID NO: 4. In a specific embodiment, the heavy chain comprises CDR1 having the sequence GFTFSFYG (SEQ ID NO: 8), CDR2 having the sequence ISGGGNYT (SEQ ID NO: 9), and CDR3 having the sequence VRAYYGNWNSY (SEQ ID NO: 10). One or both of the heavy chain and the truncated heavy chain can comprise one or more mutations in the constant region to promote dimerization of the heavy chain and the truncated heavy chain. In one embodiment, the heavy chain comprises a E356K mutation and/or a D399K mutation. In one embodiment, the truncated heavy chain comprises a K392D mutation and/or a K409D mutation. In embodiments, the monovalent anti-huFcεRIα mAb is a chimeric antibody, in which the constant region of the heavy chain is from human IgG1 (γ1) and the constant region of the light chain is from human kappa chain.

In another specific embodiment, the mv mAb comprises the heavy chain of IE7 (SEQ ID NO: 12). In another specific embodiment, the mv mAb comprises a truncated heavy chain derived from the heavy chain of IE7, having SEQ ID NO: 13: METDTLLLWVLLLWVPGSTGDKTH-TCPPCPAPELLGGPSVFLEPPKPKDTLMIS RTPE-VTCVVVDVSHEDPEVKFNWYVDGVEVHNAKTKP-REEQYNSTYRVVSVL TVLHQDWLNGKEYKCK-VSNKALPAPIEKTISKAKGQPREPQVYTLPPS-REEMTK NQVSLTCLVKGFYPSDIAVEWESNGQPEN-NYDTTPPVLDSDGSFFLYSDLTVDK SRWQQGN-VFSCSVMHEALHNHYTQKSLSLSPGK, which includes a leader sequence that is cleaved during secretion.

In embodiments, the epitope is the same epitope that is bound by the mAb IE7. In embodiments, the mAb does not compete with IgE for binding to FcεRIα. In some embodiments, the mAb binds to human FcεRIα.

Compositions and Medicaments

In one embodiment, a pharmaceutical composition comprising an anti-FcεRIα monovalent mAb of the present disclosure is provided. In certain embodiments, the pharmaceutical composition is for use in treating an allergy or desensitizing a subject to an allergen. In embodiments, the pharmaceutical composition comprises an anti-FcεRIα monovalent mAb of the present disclosure and a pharmaceutical carrier. In embodiments, the pharmaceutical composition is formulated for intravenous or subcutaneous administration.

In another embodiment, a method of use of an anti-FcεRIα monovalent mAb as described herein in the manufacture of a medicament for the treatment of an allergy is provided.

In another embodiment, a polynucleotide or combination of polynucleotides encoding the anti-FcεRIα monovalent mAb are provided.

In another embodiment, a vector comprising the polynucleotide or combination of polynucleotides is provided.

In another embodiment, a host cell comprising the polynucleotide or combination of polynucleotides is provided.

Methods of Use

In embodiments, desensitization to an allergen is accomplished by administering an anti-FcεRIα mAb. Various anti-FcεRIα mAbs are suitable for use in the presently disclosed methods. Examples of suitable mAbs include, but are not limited to, AER-37 (CRA-1), 15.1, IE7, and IB10.

In embodiments, a method of desensitizing a subject to allergen is provided, the method comprising administering to a subject with an allergy a plurality of doses of a first anti-FcεRIα mAb, wherein the doses are administered over a period of 1 to 4 days, and wherein each dose is lower than a level required to induce shock, thereby desensitizing the subject to the allergen.

In embodiments, the allergen is selected from the group consisting of protein, polysaccharide, lipid, polynucleotide, food, pollen, mold spores, dust, animal dander, insect debris, blood serum, drugs, cosmetics, and combinations thereof. In certain embodiments, the allergen is a food allergen selected from the group consisting of eggs, milk, peanuts, tree nuts, soy, sesame, crustacean shellfish, and wheat.

In embodiments, the first anti-FcεRIα mAb is a monovalent mAb. In a specific embodiment, the first anti-FcεRIα mAb is IE7. In another specific embodiment, the first anti-FcεRIα mAb is IB10.

In one embodiment, the methods disclosed herein comprise administration of a first anti-FcεRIα mAb followed by repeated equal or escalating doses of the first anti-FcεRIα mAb. In a specific embodiment, each succeeding dose is double, (i.e., 2×) the immediately preceding dose.

In another embodiment, administration of the plurality of doses of the first anti-FcεRIα mAb further comprises administering a plurality of doses of a second anti-FcεRIα mAb, wherein each dose of the second anti-FcεRIα mAb is lower than a level required to induce shock. The first anti-FcεRIα mAb and second anti-FcεRIα mAb may be administered together (i.e., co-administered). In embodiments, the total dose of anti-FcεRIα mAb co-administered is lower than a level required to induce shock. When first and second anti-FcεRIα mAbs are co-administered, each total dose of anti-FcεRIα mAb may be the same as, or higher than, each immediately preceding total dose. In a specific embodiment, each succeeding total dose is double (i.e., 2×) the immediately preceding total dose.

In embodiments, one or both of the first and second anti-FcεRIα mAbs are monovalent mAbs. In a specific embodiment, the first anti-FcεRIα mAb and the second anti-FcεRIα mAb each bind to a different epitope of FcεRIα. In a very specific embodiment, the first anti-FcεRIα mAb is IE7 and the second anti-FcεRIα mAb is IB10.

In embodiments, any of the methods disclosed herein comprise administration of a first anti-FcεRIα mAb and optionally a second anti-FcεRIα mAb in intervals, namely, at intervals such as 30 minutes, 60 minutes, 90 minutes, 2 hours, 3 hours, 4 hours, 5 hours, 6 hours, 7 hours, 8 hours, 10 hours, 12 hours, 18 hours, 24 hours, or at varying intervals. In a specific embodiment, the first anti-FcεRIα mAb is administered every 1-4 hours. In another specific embodiment, the first anti-FcεRIα mAb and the second anti-FcεRIα mAb are co-administered every 1-4 hours.

Administration of one or more anti-FcεRIα mAbs of the presently disclosed methods comprises from 4-40 administrations over a period of 1, 2, 3, or 4 days. For instance, 1, 2, 3, 4, 5, 6, 7, 8, 9, or 10 doses can be administered per day. The doses can be provided at intervals such as 30 minutes, 60 minutes, 90 minutes, 2 hours, 3 hours, 4 hours, 5 hours, 6 hours, 7 hours, 8 hours, 10 hours, 12 hours, 18 hours, 24 hours, or at varying intervals.

In embodiments, the methods of the disclosure comprise administration of a single dose of the mv anti-FcεRIα mAb disclosed herein.

Methods of the disclosure can further comprise additional doses of one or more anti-FcεRIα mAbs at intervals of 1, 2, 3, 4, 6, 8, or 12 weeks or of 1, 2, 3, 4, 5, or 6 months following the last repeated equal or escalating dose of the anti-FcεRIα mAb, or following the single dose of the mv anti-FcεRIα mAb.

Each dose of the anti-FcεRIα mAb is lower than a level required to induce shock in the subject. In one embodiment, the dose can be about ½ the level required to induce shock in the subject. In another embodiment, the dose can be less than about ½ the level required to induce shock in the subject, for example, about ⅓, ¼, ⅕, ⅙, ⅐, ⅛, ⅒, 1/16, 1/20, or 1/25 the level required to induce shock in the subject.

In another embodiment, a method of desensitizing a subject to an allergen is provided, the method comprising administering to a subject with an allergy a first dose of a first anti-FcεRIα mAb at a dose that is lower than a level required to induce shock, wherein the first anti-FcεRIα mAb is a monovalent anti-FcεRIα mAb according to the present disclosure, thereby desensitizing the subject to the allergen.

In embodiments, the method further comprises subsequently administering a second dose of the first anti-FcεRIα mAb at a dose that is lower than a level required to induce shock. In embodiments, the method further comprises administering additional doses of the first anti-FcεRIα mAb every 1-4 weeks, wherein each additional dose is lower than a level required to induce shock.

In another embodiment, the method further comprises subsequently administering a first dose of a second anti-FcεRIα mAb at a dose that is lower than a level required to induce shock. Optionally, the method comprises co-administering a second dose of the first anti-FcεRIα mAb with the first dose of the second anti-FcεRIα mAb, wherein the total dose of anti-FcεRIα mAb is lower than a level required to induce shock. In embodiments, the first dose of the second anti-FcεRIα mAb is administered about 24 hours after the first dose of the first anti-FcεRIα mAb.

In embodiments, the method further comprises administering additional doses of the second anti-FcεRIα mAb every 1-4 weeks, wherein each additional dose is lower than a level required to induce shock. In another embodiment, the method further comprises co-administering additional doses of the first anti-FcεRIα mAb and the second anti-FcεRIα mAb every 1-4 weeks, wherein each additional total dose of anti-FcεRIα mAb is lower than a level required to induce shock.

Methods of treating an allergy and methods of preventing an allergic reaction in a subject having an allergy are provided, comprising administration of one or more anti-FcεRIα mAbs as described herein, and according to the dosing schedules described herein. In specific embodiments, the allergic reaction is anaphylaxis.

Embodiments of the present disclosure are further defined by reference to the following non-limiting examples. It will be apparent to those skilled in the art that various modifications, both to materials and methods, can be practiced without departing from the scope of the present disclosure.

EXAMPLES

Example 1. Adaptation of Anti-FcεRIα Rapid Desensitization (RD) to Humans

The present inventors previously reported that mice can be rapidly desensitized (RD' d) with MAR-1, a hamster IgG mAb that binds mouse FcεRIα that is not associated with IgE. See Khodoun et al., J. Allergy Clin. Immunol. 133: 1555-1564 (2013). Although a single large dose of MAR-1 caused anaphylaxis, administering MAR-1 by a RD approach did not induce anaphylaxis. RD with MAR-1 rapidly induced short-lived mast cell anergy. Continued treatment with MAR-1 removed all IgE from mast cells over several days. Once RD with MAR-1 was performed, mast cell loss of IgE could be safely maintained by repeated, large doses of MAR-1. RD with MAR-1 completely suppressed IgE-mediated anaphylaxis in passive and active sensitization models, suppressed established IgE-mediated food allergy, and was antigen-non-specific. In addition, RD with MAR-1 was safer and its effects longer-lasting than rapid desensitization with antigen in mice that had been sensitized to that antigen by active immunization.

To determine if this approach could be adapted to humans, the studies used (1) anti-human (hu) FcεRIα mAbs and (2) mice whose mast cells and basophils express huFcεRIα. For the first purpose, hybridoma 15.1 was obtained, which produces a mouse IgG1 mAb that, like MAR-1, competes with IgE for binding to FcεRIα. AER-37 (also called CRA-1) was purchased, a mouse IgG2b mAb that binds huFcεRIα regardless of its association with IgE. Mouse IgG1 mAbs to huFcεRIα was produced by immunizing FcεRIα-deficient BALB/c mice with huFcεRIα. One of these mAbs, IE7, does not compete with IgE (or 15.1) for binding to huFcεRIα but competes with AER-37; another of these mAbs, D310, has the opposite characteristics. See U.S. Pat. No. 10,086,005. For the second purpose, acquired BALB/c mice that lack mouse FcεRIα and express a hu FcεRIα transgene were acquired. In these "huFcεRIα mice," a functional receptor is formed that includes huFcεRIα chain, mouse FcεRIβ chain, and mouse FcεRIγ chains. NSGS and NRGS mice were reconstituted, which lack T, B, and NK cells, and express transgenic huSCF, huIL-3 and huGM-CSF, with T cell-depleted human cord blood cells. Stem cells in the donor cell population generate hu B cells, T cells, basophils, mast cells and myeloid cells in these "reNSGS" and "reNRGS" mice in 2-3 months. (NRGS mice have non-functional RAG1 alleles, instead of the SCID alleles in NSGS mice.)

Figure 2:
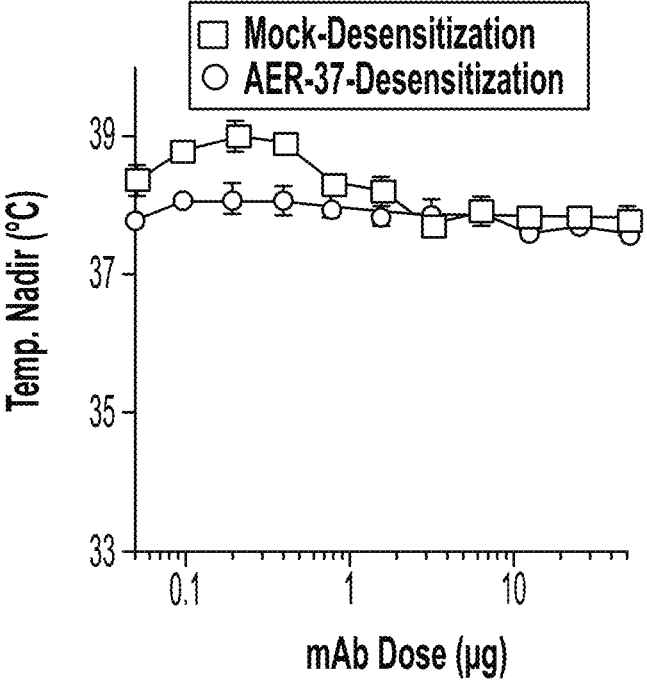
FIG. 2 shows that RD with AER-37, an anti-huFcεRIα mAb that does not compete with IgE for binding to huFcεRI, suppresses anaphylaxis induction by challenge with a large dose of the same mAb. HuFcεRIα mice (4/group) were mock-desensitized with an isotype-control mAb or rapidly desensitized with AER-37, starting with a dose of 50 ng i.p. and doubling that dose hourly until a dose of 50 μg was reached. The lowest rectal temperatures during the hour following each dose of AER-37 or control mAb are shown.
Figure 3:
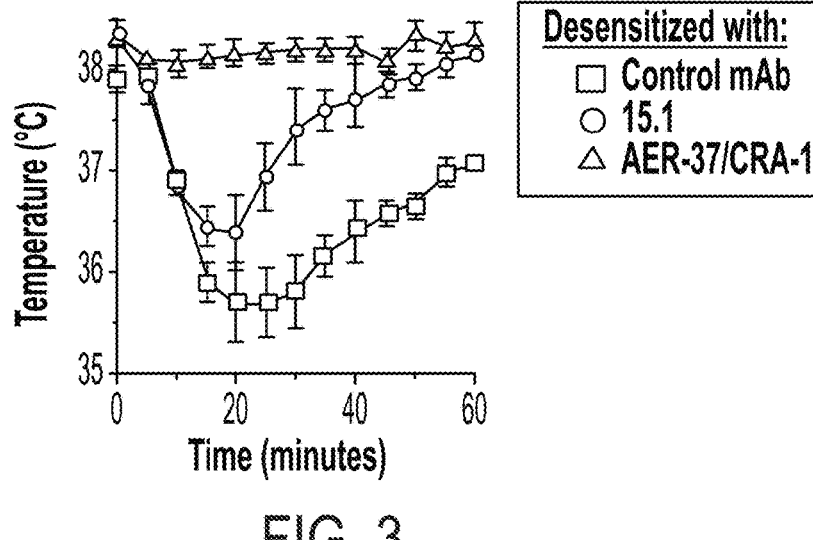
FIG. 3 shows that RD of huIgE-primed huFcεRIα mice with anti-huFcεRIα mAb blocks anti-huIgE mAb-induced anaphylaxis. HuFcεRIα mice (4/group) were sensitized with huIgE anti-trinitrophenyl (TNP) mAb, then rapidly desensitized with 15.1, an anti-huFcεRIα mAb that competes with IgE for binding to huFcεRI, or with AER-37, as in FIG. 2, and challenged 24 hours later with anti-huIgE mAb. Decreases in rectal temperature were determined for the hour after challenge. Temperature drops were significantly different among all 3 groups.

Initial studies with mAbs 15.1 and AER-37 in huFcεRIα mice showed that a single large dose of either mAb induces anaphylaxis, with AER-37 causing more severe disease (FIG. 1). However, RD prevented their induction of anaphylaxis, even when a final dose of 50 μg of anti-FcεRIα mAb was given (FIG. 2). In huFcεRIα mice that had been pre-sensitized with huIgE, RD with AER-37 completely prevented anti-huIgE mAb-induced anaphylaxis (FIG. 3). RD of huIgE-sensitized huFcεRIα mice with AER-37 more quickly and effectively prevented IgE-mediated anaphylaxis than treatment with the anti-huIgE mAb, omalizumab, which selectively binds IgE that is not associated with FcεRI. RD with mAb 15.1 was equally safe but less effective than RD with AER-37, presumably because, like omalizumab, it does not remove FcεRI-associated IgE.

Figure 4:
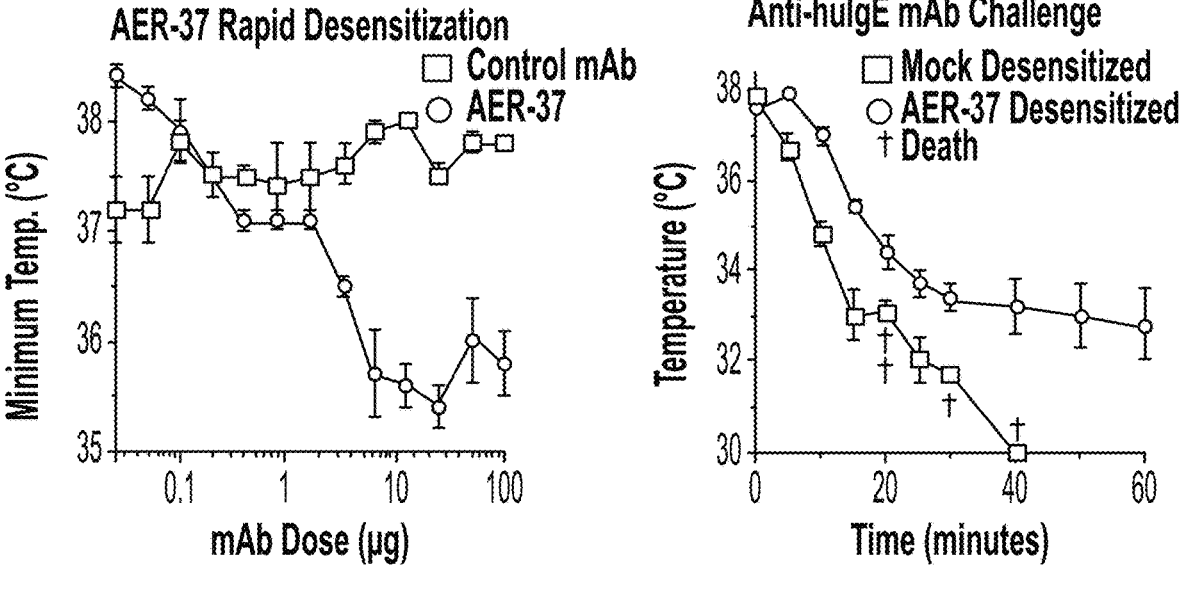
FIG. 4 shows that RD with AER-37 partially protects reNRGS mice against anaphylaxis. reNRGS mice are immunodeficient, human IL-3/GM-CSF/SCF-producing NRGS mice that have been reconstituted with human cord blood and have developed human basophils and mast cells. reNRGS mice (4/group) were sensitized with recombinant huIgE anti-TNP mAb, then mock-desensitized or RD'd with the hourly i.p. mAb dose shown, starting with 20 ng and ending with 100 μg. Minimum rectal temperatures during the hour following each dose of AER-37 or control mAb (left panel) and the response to anti-huIgE mAb challenge 1 day after completing desensitization (right panel) are shown.
Figures 5, 6:
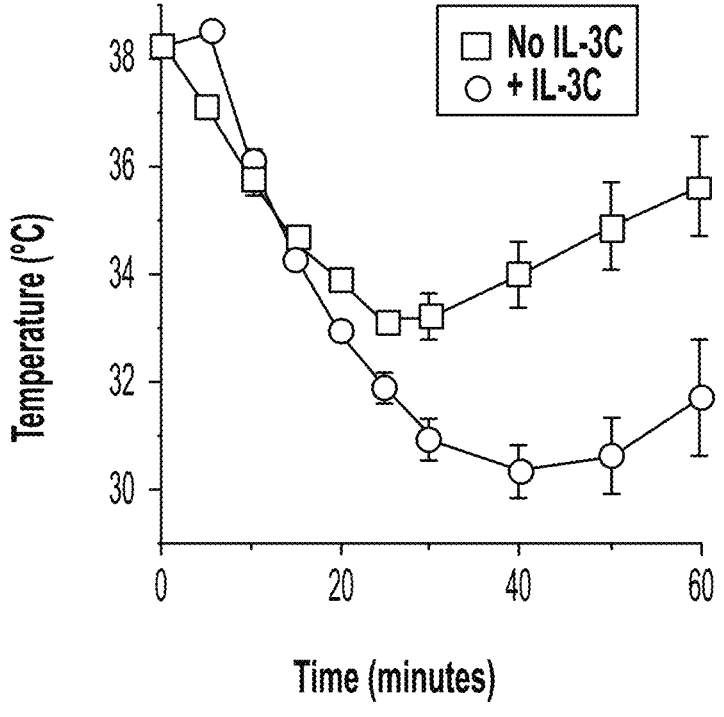
FIG. 5 shows that IL-3 exacerbates antigen-induced, IgE-mediated anaphylaxis. BALB/c mice (4/group) were sensitized with IgE anti-TNP mAb and injected i.v. with saline or with mouse IL-3C, a long acting form of mouse IL-3, produced by mixing 50 μg of 8F8 rat-anti-mouse IL-3 mAb plus 10 μg of mouse recombinant IL-3 (1:2 molar ratio). The next day, mice were injected i.v. with 10 μg of TNP-OVA to crosslink IgE/FcαRI on mast cells and basophils, and followed for development of hypothermia. Differences between groups are statistically significant.
FIG. 6 shows that RD of reNRGS mice partially suppresses the mast cell $Ca^{++}$ response to antigen challenge. reNRGS mice were sensitized with IgE anti-TNP mAb, then mock desensitized or RD'd with AER-37 (max. dose 50 μg). The next day, peritoneal mast cells were Fluo-4-loaded and challenged with TNP-OVA or PMA+ionomycin and analyzed for intracellular $Ca^{++}$. Percent inhibition by RD is shown. Data is pooled from 2 experiments, 8 mice/group. Inhibition is significant.

Anti-huFcεRIα mAb RD of actively sensitized huFcεRIα/F709 mice and passively sensitized reNSGS and reNRGS mice was more difficult than RD of passively sensitized huFcεRIα mice. Challenge of reNSGS mice with TNP-BSA (after mouse IgE anti-TNP mAb sensitization) or with only 200 ng of anti-huIgE mAb induced fatal anaphylaxis (FIG. 4, right panel). RD of these mice with AER-37 prevented lethal anti-FcεRIα mAb-induced anaphylaxis, but still caused hypothermia (FIG. 4, left panel) and these mice still developed non-lethal anaphylaxis in response to anti-huIgE mAb challenge (FIG. 4, right panel). Similar results were observed with actively sensitized huFcεRIα/F709 mice. Two possible explanations for the incomplete protection provided by RD in reNSGS and reNRGS mice are their large numbers of mast cells (10-200 times the number in WT mice) and their high levels of IL-3 and SCF, which amplify the ability of antigen crosslinking of IgE/FcεRI to induce mast cell degranulation (FIG. 5). An attempt to rapidly desensitize reNSGS mice with AER-37 demonstrated significant, but incomplete suppression of the Ca$^{++}$ response to antigen challenge (FIG. 6).

Example 2. Gradual Desensitization with Repeated Small Doses of Anti-FcεRIα mAb Suppresses Anaphylaxis To determine if slower, more gentle desensitization could more safely and completely protect reNRGS and huFcεRIα/F709 mice, investigators first determined whether huFcεRIα mice could be fully desensitized by repeated injection of very low doses of the anti-huFcεRIα mAb, IE7, instead of injecting escalating doses of this mAb. Six hourly 400 ng doses of IE7 removed nearly all IgE and most FcεRI from mast cells in huFcεRIα mice and blocked the anaphylactic response to injection of 200 μg of IE7 (FIG. 7), but only partially desensitized reNRGS mice.

Figure 8:
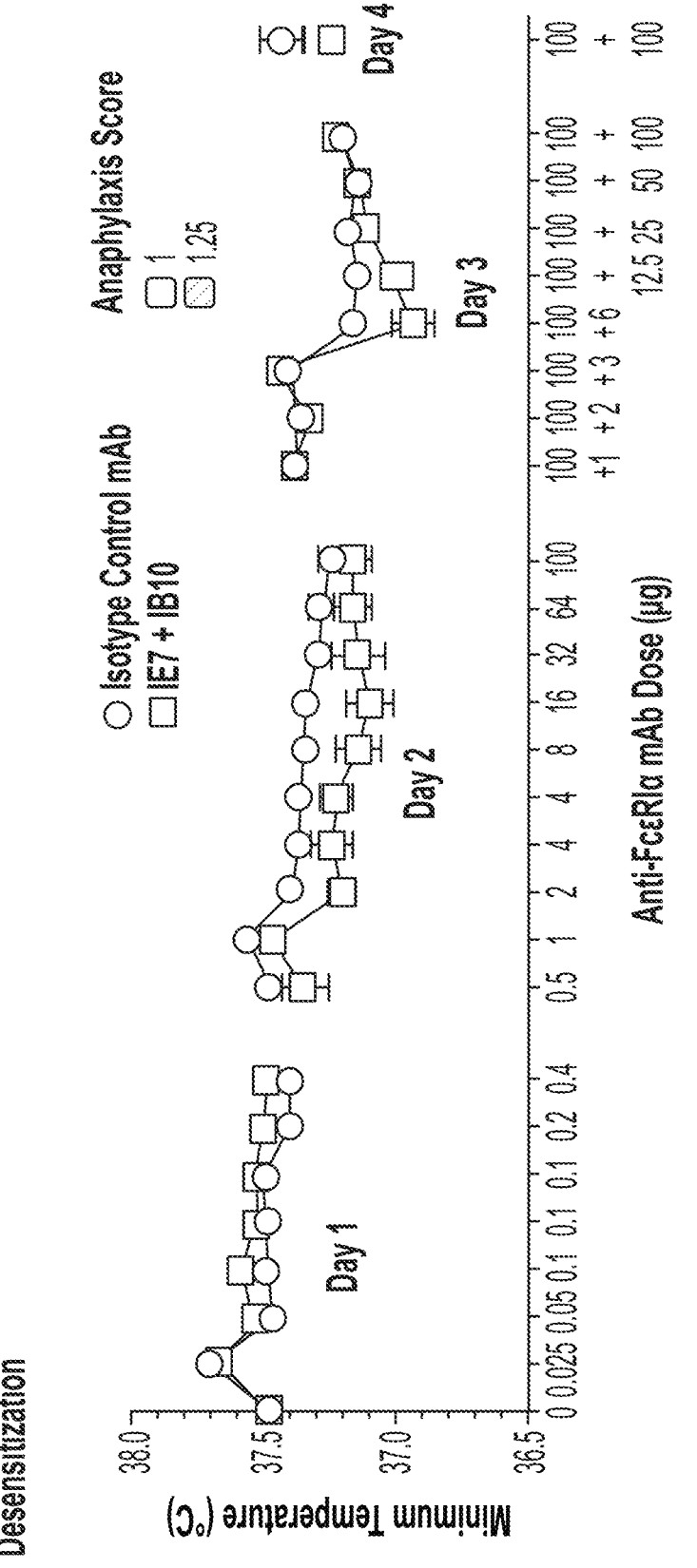
FIG. 8 shows that less rapid desensitization of reNRGS mice with anti-FcεRIα mAbs IE7 and IB10 is safe and effective. ReNRGS mice were sensitized with huIgE anti-TNP mAb daily×4 days and desensitized for 3 successive days by hourly i.p. injection of the doses of IE7 or IE7+ IB10, shown along the abscissa of the upper panel (single numbers indicated dose of IE7; numbers separated by a "+" indicate doses of IE7 and IB10). IE7+IB10-treated mice developed little or no hypothermia as compared to isotype control mAb-treated mice and no changes in activity. One hour after the last doses of IE7+IB10, mice were challenged i.v. with TNP-OVA and followed for the next hour for drop in survival and drop in rectal temperature (lower left panel). Splenic mast cells from additional desensitized mice were stained (lower middle panel) for IgE, saturation with IE7 (staining with AER-37) or FcεRIα that is not associated with IgE (staining with 15.1). Peritoneal mast cells from these mice were stained for IgE (lower right panel).
Figure 8:
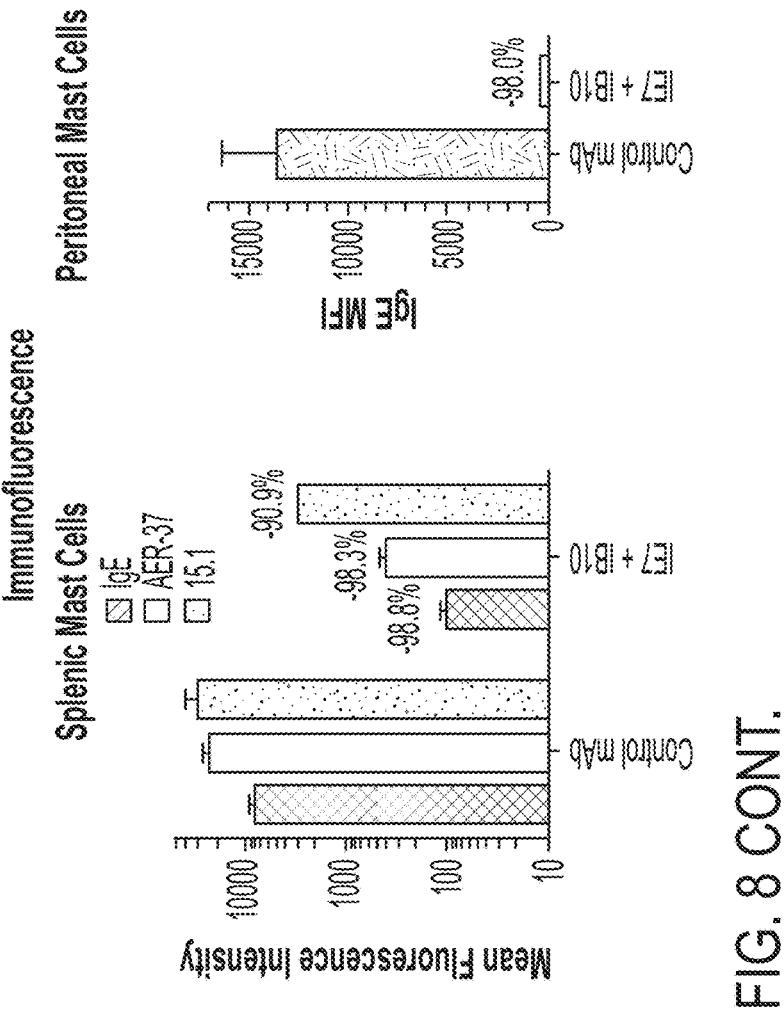
Figure 8:
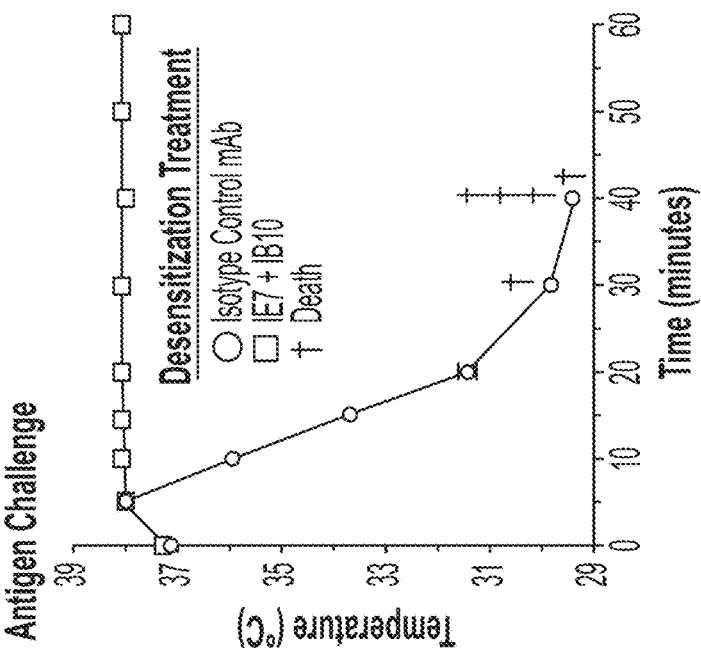

The success in huFcεRIα mice led the present investigators to try a 3-day desensitization protocol in reNRGS mice that treated them with repeated low doses of IE7, followed by increasing doses of IE7, then IB10 (a mouse IgG1 mAb that, like 15.1, competes with IgE for binding to huFcεRIα). This approach did not cause hypothermia during desensitization, removed >98% of IgE from peritoneal and splenic mast cells and 91% of FcεRIα from splenic mast cells, and protected reNRGS mice against IgE-mediated, antigen-induced anaphylaxis (FIG. 8). Very similar results were obtained for RD of actively immunized huFcεRIα/F709 mice.

Figure 7:
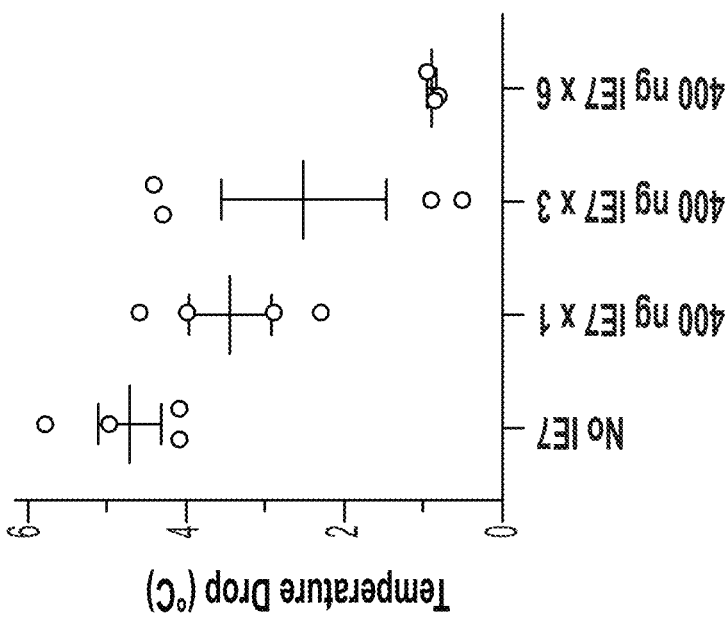
FIG. 7 shows that repeated small anti-FcεRIα mAb doses suppress anaphylaxis. Left panels: HuFcεRIα mice were injected i.p. with 1 or 6 hourly 400 ng doses of IE7. One hour after the last dose, peritoneal cells were stained for IgE (top) and FcεRIα (bottom; with 15.1, which is not blocked by IE7). Right panel: Additional mice were injected i.p. with 1-6 hourly 400 ng doses of IE7 mAb. One hour after the last dose, mice were challenged with 200 μg of IE7 and followed for 1 hour for hypothermia. Maximum temperature drops for each mouse (4/group) are shown with group means and SEMs.
Figure 7:
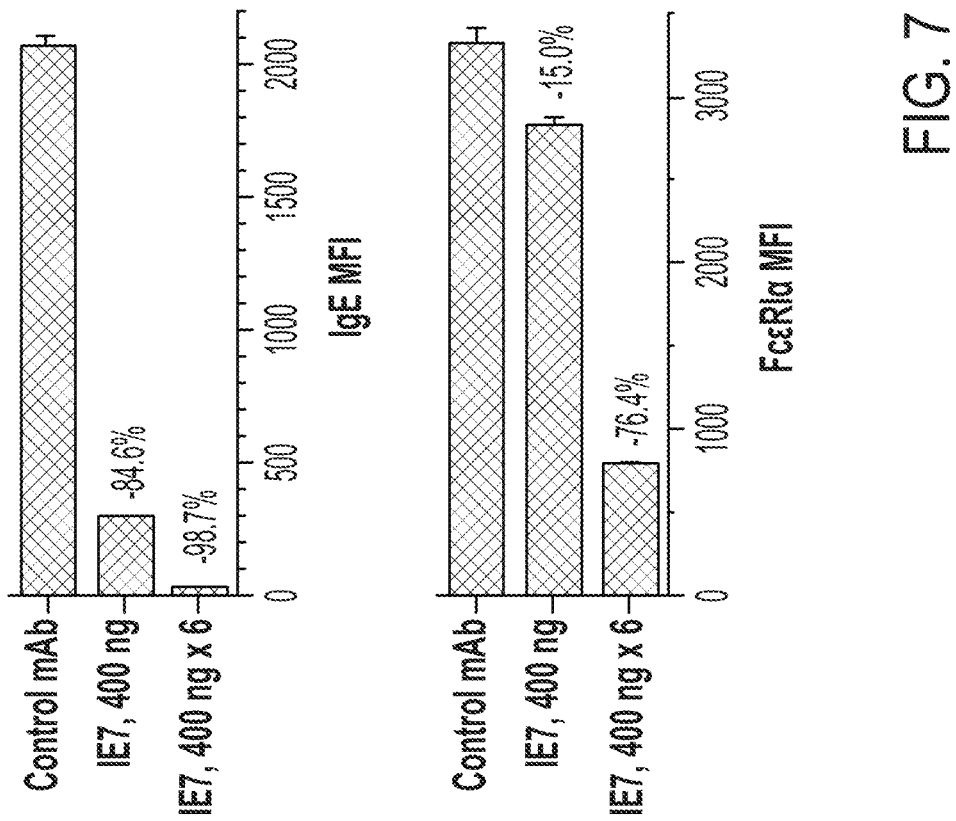

The greater loss of IgE than FcεRI by mast cells in anti-FcεRIα mAb-treated mice has been consistent and is particularly marked when mice are treated for a limited time with a low dose of AER-37 or IE7 (FIG. 7). Thus, although AER-37 and IE7 do not suppress IgE binding to mast cell FcεRI in vitro, they must cause a change in the structure or cellular distribution of FcεRIα in vivo that limits its binding of IgE.

Example 3. Use of a Monovalent Anti-huFcεRIα Monoclonal Antibody for RD

Because IgE-mediated mast cell/basophil degranulation requires FcεRI crosslinking, injecting mice with sufficient mv anti-FcεRIα mAb might saturate the FcεRIα epitopes recognized by that mAb without crosslinking FcεRI sufficiently to induce mast cell degranulation. If so, a mv mAb might delay the binding of subsequently injected dv mAb to the same epitope sufficiently for the dv mAb to cause desensitization without degranulation. Alternatively, mv anti-FcεRIα mAb might indirectly crosslink basophil and mast cell FcεRI, through other mechanisms, which could cause these cells to become less responsive to FcεRI crosslinking (i.e.; to become anergic) and remove some or all of their IgE. As a third possibility, mv anti-FcεRIα mAb might be retained on the basophil/mast cell surface long enough to mediate complement-mediated cytotoxicity or antibody-dependent cell mediated cytotoxicity (ADCC).

Figure 9:
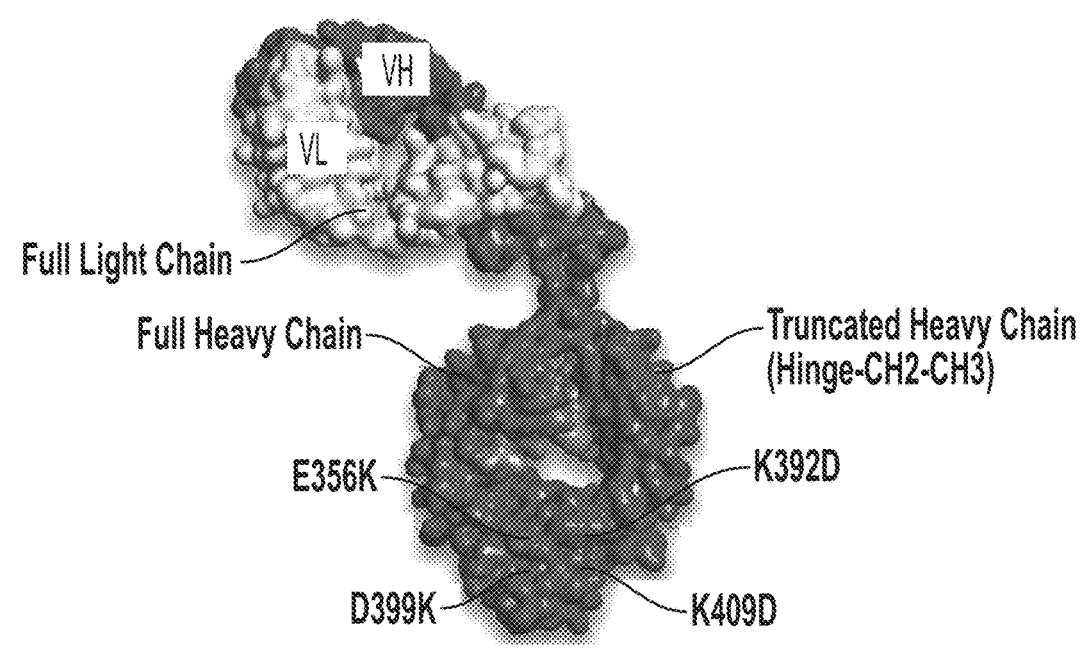
FIG. 9 shows the structure of monovalent (mv) huIgG1 IE7. This model shows the single complete κ chain, complete heavy chain, and truncated heavy chain (which lacks VH and CH1), which combine to form a mv version of IE7. The V region domains are derived from IE7, a mouse IgG1 mAb that binds huFcεRIα regardless of whether FcεRI has bound IgE. The C region domains are derived from hu κ and $\gamma_1$ chains. The two mutations each in the complete and truncated heavy chains create electrostatic steering effects that promote preferential binding of the complete and truncated hu$\gamma_1$ chains to each other to create heterodimers.
Figure 10:
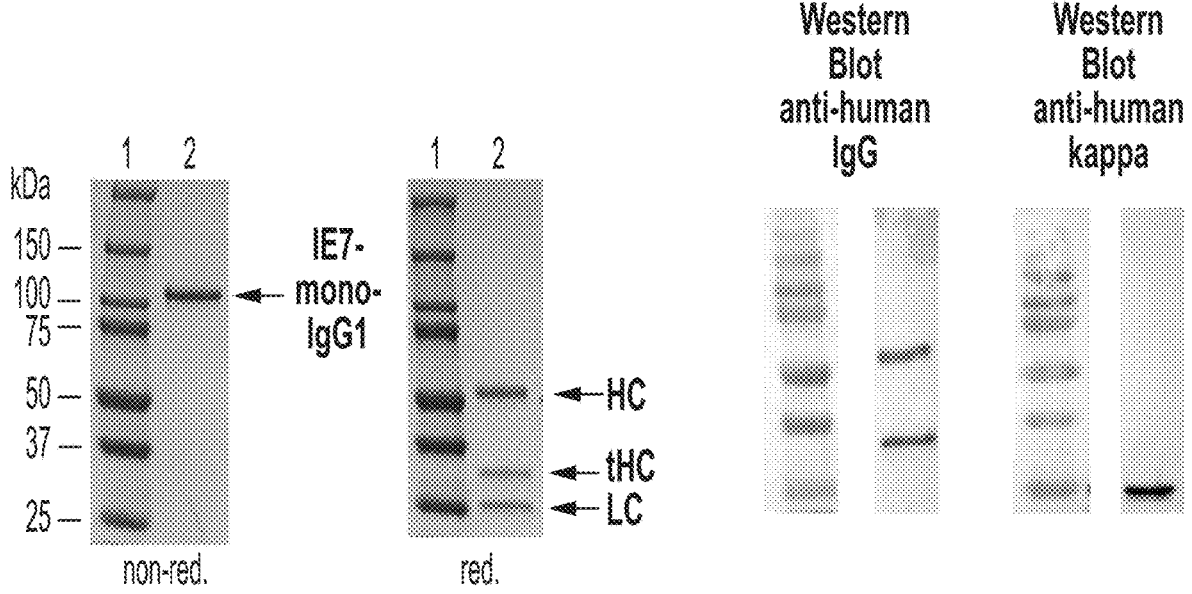
FIG. 10 shows biochemical characterization of purified mv huIgG1 IE7. SDS-PAGE of non-reduced (non-red.) and reduced (red.) purified mv huIgG1 IE7 is shown in the two photos on the left; Western blots of reduced purified mv huIgG1 IE7 with anti-huIgG1 Ab and anti-hu κ Ab are shown in the two photos on the right. HC=heavy chain; tHC=truncated heavy chain; LC=light (κ) chain.

To evaluate these possibilities, a mv version of IE7 composed of one κ chain, one complete heavy chain that has $hu\gamma_1$ constant and hinge regions, and one truncated $hu\gamma_1$ chain that lacks V and $CH_1$ regions was designed and produced (FIG. 9). Mutations in the complete $hu\gamma_1$ chain (E356K and D399K) and the truncated $hu\gamma_1$ chain (K392D and K409D) create electrostatic steering effects that promote preferential binding of the complete $hu\gamma_1$ chain to the truncated $hu\gamma_1$ chain to create heterodimers. A 3-step purification process uses affinity chromatography to select for $hu\gamma_1$ chain $CH_1$ and huκ chain, and size exclusion chromatography to eliminate any contaminating free $hu\gamma_1$ chains, and Ab aggregates. The purified 3-chain molecule had the expected apparent molecular weight by SDS-PAGE, with no detectable dv Ab (FIG. 10).

Figure 11:
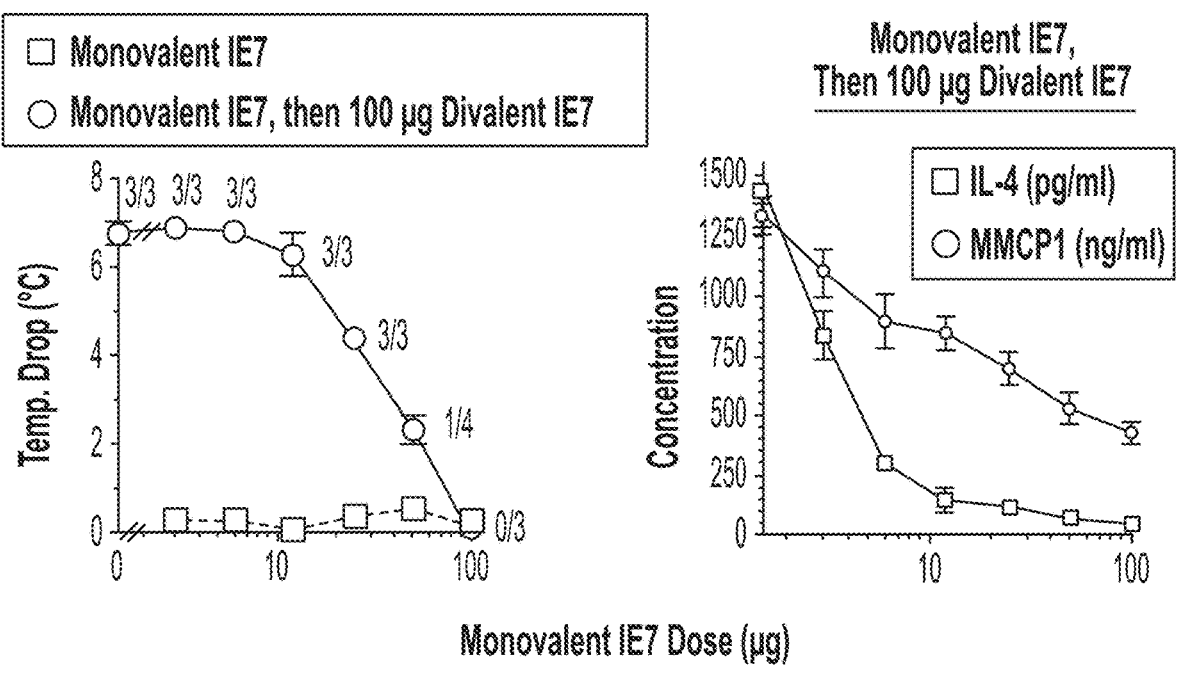
FIG. 11 shows that mv huIgG1 IE7 does not induce anaphylaxis and dose-dependently prevents divalent (dv) huIgG1 IE7-induced anaphylaxis. Left panel: Hu FcεRIα mice (3-4/group) were injected i.v. with mv huIgG1 IE7 doses shown and challenged i.v. the next day with 100 μg of dv huIgG1 IE7. Maximum rectal temperature drops during the hour after each IE7 injection are shown. Fractions indicate mice with slowed movement after dv huIgG1 IE7 injection (no mice slowed after mv huIgG1 injection). Right panel: Serum MMCP1 and IL-4 level 4 hours after dv huIgG1 IE7 injection.
Figure 12:
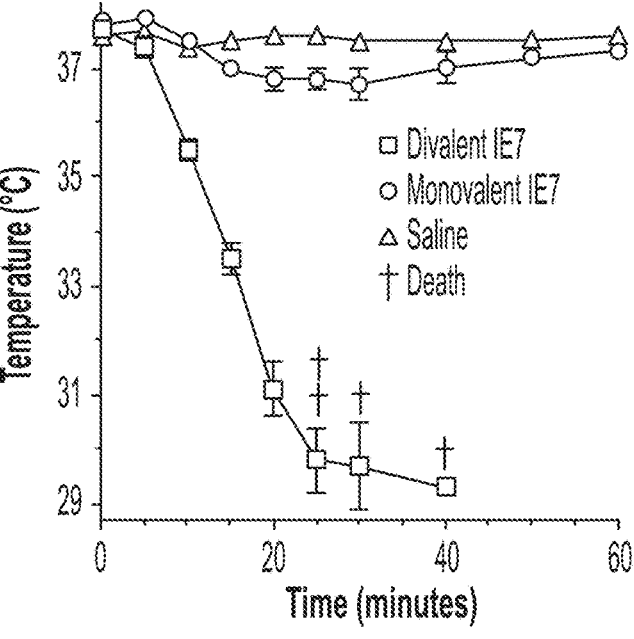
FIG. 12 shows that mv huIgG1 IE7 has little ability to induce anaphylaxis in mice that are highly sensitive to FcεRI crosslinking. HuFcεRIα mice (4/group) were injected with IL-4/anti-IL-4 mAb complexes (a long-acting formulation of IL-4) on day 0, and with the β-adrenergic receptor inhibitor propranolol on day 1, then challenged i.v. with saline (negative control) or with 100 μg of mv huIgG1 IE7 or dv huIgG1 IE7 30 minutes after the propranolol injection. Mice were followed for rectal temperature and survival for the next 60 minutes. None of the mv huIgG1 IE7-injected mice showed decreased spontaneous movement, while all of the dv huIgG1 IE7-injected mice stopped moving before they died.
Figure 13A:
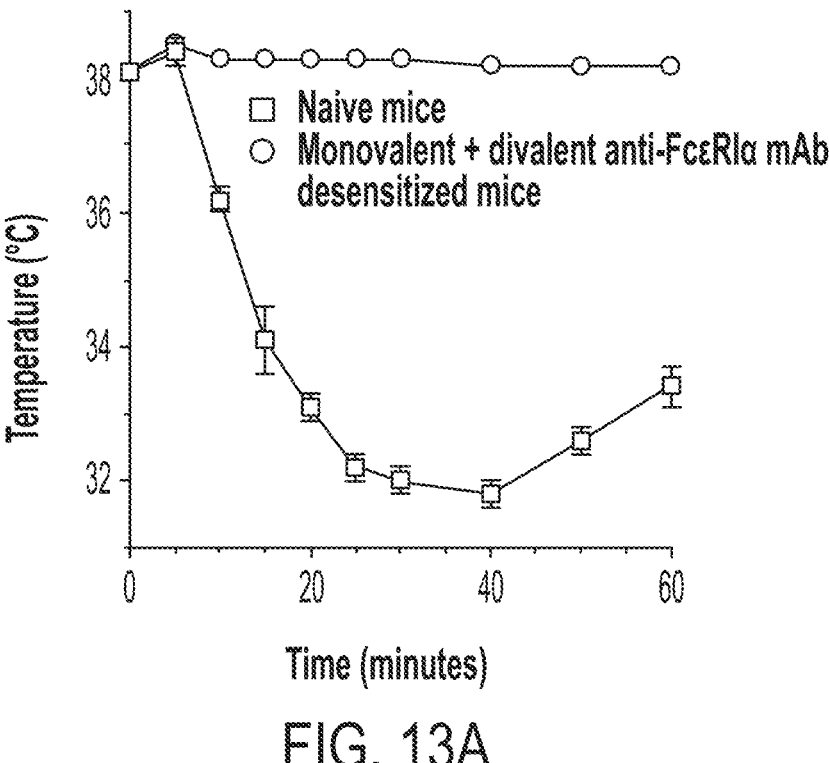
FIG. 13A shows that treatment with mv huIgG1 IE7, followed by dv huIgG1 IE7, prevents antigen-induced anaphylaxis in huFcεRIα mice. HuFcεRIα mice (4/group) were injected daily with IgE anti-TNP mAb, starting on day 0, and were mock-desensitized (naïve mice) or were desensitized with injection of 50 or 100 μg of mv huIgG1 IE7 on day 1 and with 100 μg of dv huIgG1 IE7 on day 2. On day 3, all of the mice were injected i.v. with 10 μg of TNP-OVA. Rectal temperatures were followed for the next 60 minutes.
Figure 13B:
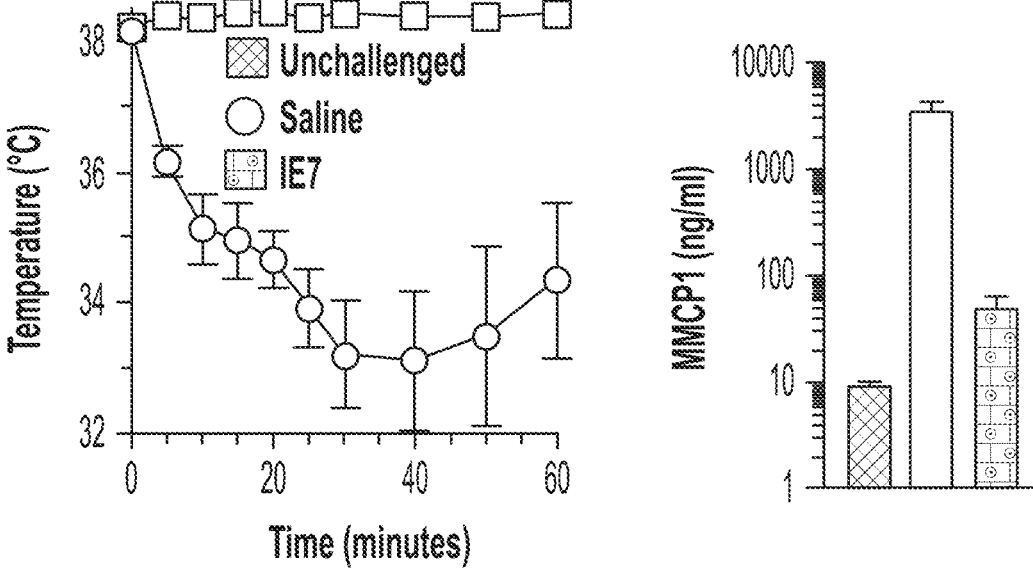
FIG. 13B shows that repeated injection of IE7 anti-FcεRIα mAb maintains protection against IgE-mediated anaphylaxis.

Injection of huFcεRIα mice i.v. with 3-100 μg of mv huIgG1 IE7 failed to induce hypothermia or any detectable change in mouse behavior (FIG. 11), while injection with 3 or more μg of dv IE7 caused anaphylaxis with severe hypothermia. Challenging previously untreated huFcεRIα mice i.v. with 100 μg of dv huIgG1 IE7 caused an ~7° C. drop in rectal temperature; however, pre-treatment with mv huIgG1 IE7 provided dose-related protection, with complete protection in mice that had received 100 μg of mv huIgG1 IE7 (FIG. 11, left panel). Mucosal mast cell degranulation (shown by serum MMCP1 level) and basophil IL-4 secretion (shown by in vivo cytokine capture assay (IVCCA)) were reduced by 68% and 97%, respectively, during the 4-hour post-i.v. challenge with dv huIgG1 IE7 in mice that had received 100 μg of mv huIgG1 IE7 prior to challenge; these reductions were mv huIgG1 IE7 dose-related (FIG. 11, right panel). Mice that were made 50-fold more sensitive to FcεRI crosslinking by pretreatment with IL-4 and propranolol developed only an ~1° C. temperature drop after i.v. challenge with 100 μg of mv huIgG1 IE7 in this experiment, although temperature drops of up to 4° C. were observed in other experiments, while i.v. injection of 100 μg of dv huIgG1 IE7 caused lethal anaphylaxis (FIG. 12).

huFcεRIα mice treated with 50 or 100 μg of mv IE7, followed by 100 μg of dv IE7, were completely protected against anaphylaxis when sensitized with mouse IgE anti-TNP mAb and challenged i.v. with TNP-ovalbumin (OVA) (FIG. 13A). Protection against IgE-mediated anaphylaxis could be safely extended for at least 2 weeks, with no adverse effects. A single dose of mv huIgG1 IE7 was followed by i.v. 100 μg doses of dv huIgG1 IE7 every 3-4 days for 18 days. Additional mice were injected with saline instead of mv or dv IE7. All mice were also injected i.v. weekly with IgE anti-TNP mAb to maintain sensitization to TNP. Mice were challenged with 50 μg of TNP-OVA i.v., and rectal temperatures were followed for the next 60 minutes (FIG. 13B, left panel). These mice and a group of totally nave huFcεRIα mice were bled 4 hours after the TNP-OVA challenge and their sera were assayed by ELISA for MMCP1 concentration (FIG. 13B, right panel). One 100 μg dose of mv huIgG1 IE7, followed by biweekly 100 μg doses of dv IE7, provided 99% suppression of the MMCP1 response to i.v. antigen challenge.

Figure 14:
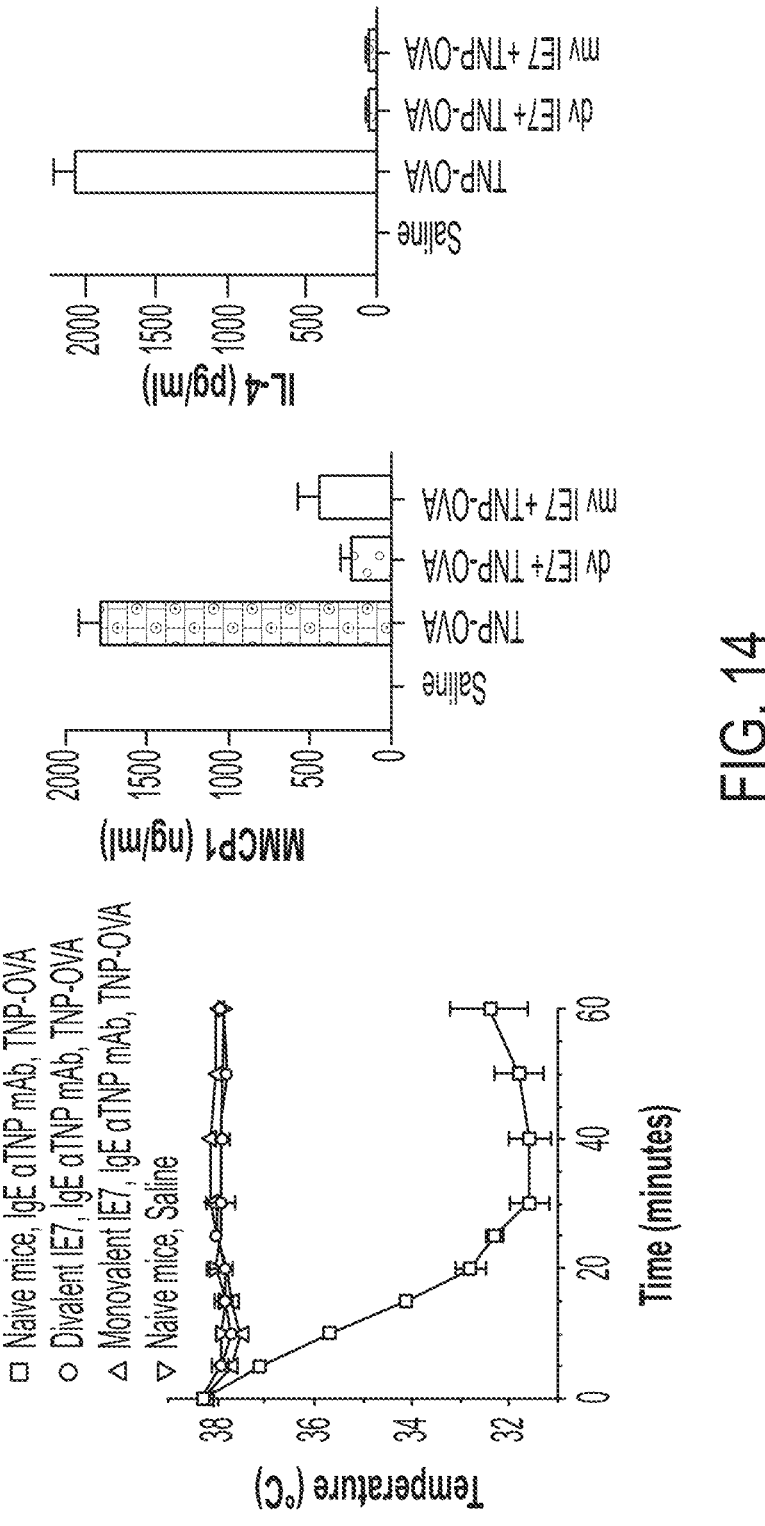
FIG. 14 shows that mv huIgG1 IE7 protects huFcεRIα mice against antigen-induced IgE-mediated anaphylaxis. HuFcεRIα mice (3-4/group) were sensitized with IgE anti-TNP mAb, then injected i.v. with saline (naïve mice) or 100 μg of mv or dv huIgG1 IE7. The next day, mice were challenged i.v. with TNP-OVA or saline and followed for the next 60 minutes for rectal temperature. All mice were bled 4 hours after challenge and IL-4 and MMCP1 responses were determined by IVCCA and ELISA, respectively.
Figure 15:
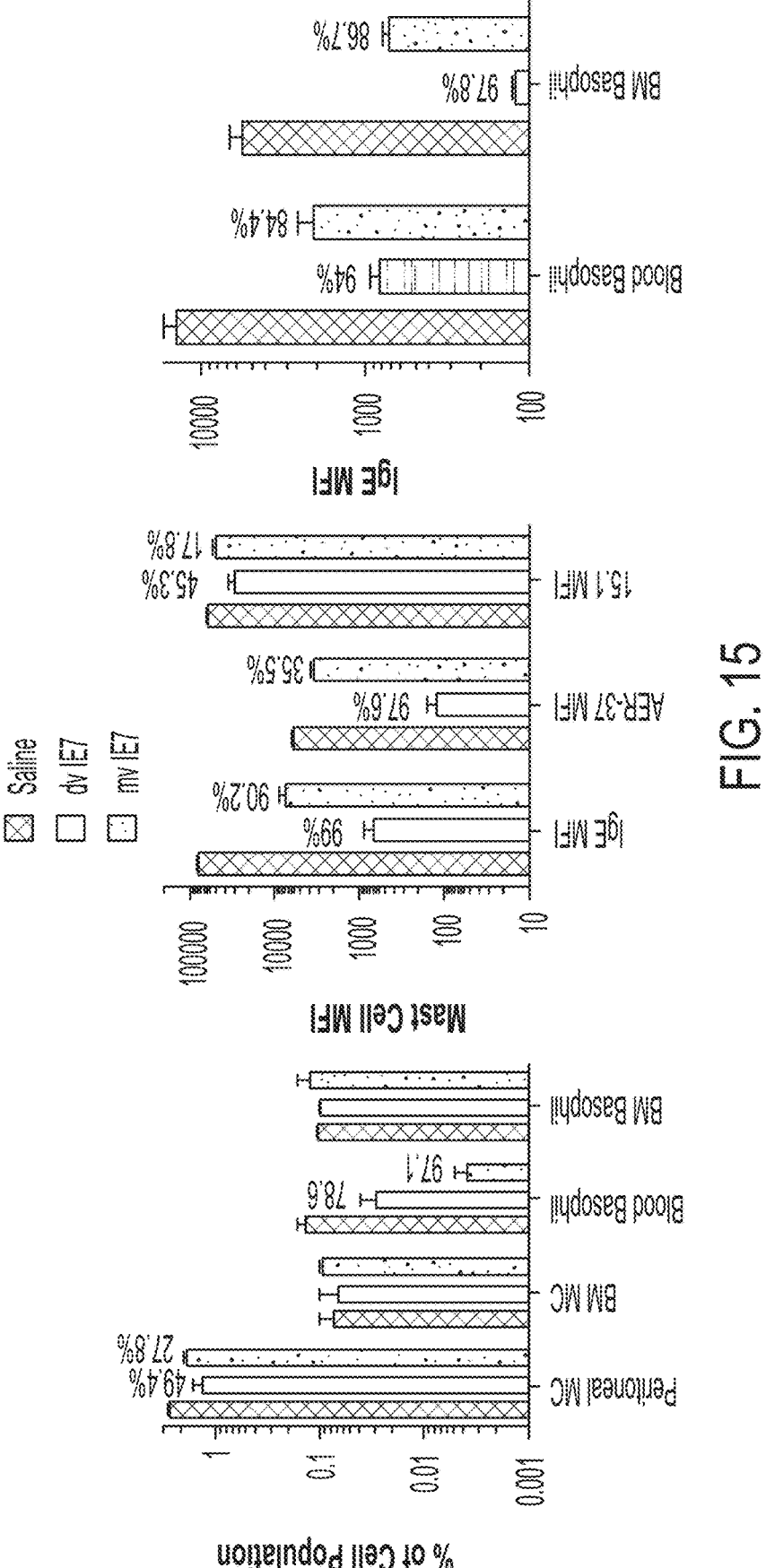
FIG. 15 shows the effects of mv and dv IE7 on basophil and mast cell number and IgE and FcεRI expression. Mv huIgG1 IE7 depletes blood basophils and removes IgE from basophils and mast cell in vivo. HuFcεRIα mice (3/group) were injected i.v. and i.p. with 10 μg of mouse IgE anti-TNP mAb and 1 day later injected i.v. and i.p. with saline or 100 μg of dv or mv huIgG1 IE7 and analyzed 1 day after that for percentages of blood, peritoneum, and bone marrow (BM) mast cells and/or basophils and their expression of IgE and staining with AER-37 or 15.1. Percentage decreases as compared to saline-injected mice are shown above bars.

Surprisingly, treating IgE anti-TNP mAb-sensitized huFcεRIα mice with 100 of mv huIgG1 IE7, without subsequent dv huIgG1 IE7, protected them nearly as well as 100 μg of dv huIgG1 IE7 against TNP-OVA challenge (FIG. 14). Consistent with this, injection of huFcεRIα mice with 100 μg of mv huIgG1 IE7 decreased peritoneal mast cell IgE expression by 90% (vs. 99% for the same dose of dv huIgG1 IE7), even though mv huIgG1 IE7 was only bound to 36% of peritoneal mast cell FcεRIα (vs. 98% for dv huIgG1 IE7) (AER-37 MFI); mv and dv huIgG1 IE7 decreased mast cell expression of FcεRIα that was not IgE-bound (15.1 MFI) by only 18% and 45%, respectively (FIG. 15). Because anti-huFcεRIα mAb probably removes mast cell IgE by redistributing, rather than simply binding to FcεRI (IE7 does not remove mast cell IgE in vitro at 4° C.), and Abs initiate redistribution of surface molecules by crosslinking them, mv huIgG1 IE7 most likely has some ability to crosslink FcεRI. In this regard, the IgE-removing effect of treatment with a single, relatively large dose of mv huIgG1 IE7 appears to resemble that of repeated low doses of dv IE7 (FIG. 7), with the addition that a single 100 μg dose of mv mAb should saturate mast cell FcεRI more than repeated 400 ng doses of dv mAb.

Both mv and dv huIgG1 IE7 modestly reduced mast cell percentages in the peritoneum in this experiment (but had no effect on peritoneal mast cell percentages in other experiments) and depleted blood basophils, but did not decrease percentages of BM mast cells or basophils, although they considerably reduced IgE on both basophil populations (FIG. 15) and on BM mast cells. Because repeated low doses of dv IE7 protect reNRGS mice less well than huFcεRIα mice against IgE-mediated anaphylaxis, the investigators explored whether mv huIgG1 IE7 protects reNRGS mice. In one experiment, mv huIgG1 IE7 injection did not induce hypothermia in two huIgE anti-TNP-sensitized reNRGS mice and completely protected them against i.v. TNP-OVA. However, there was only a 7° C. temperature drop in the single non-desensitized, huIgE anti-TNP mAb-sensitized reNRGS mouse that was challenged i.v. with TNP-OVA, and that mouse died after a few hours rather than in <30 min; this result suggests that these mice had fewer human mast cells than usual.

Taken together, these results support the conclusion that the mv anti-huFcεRIα mAb is safe and efficacious because it simultaneously binds FcεRI and FcγRs. This produces slow but persistent FcεRI crosslinking, which is insufficient to induce substantial rapid mast cell degranulation, but sufficient to suppress mast cell signaling and remove mast cell IgE. The surprising result that mv huIgG1 IE7 is more effective than the dv form of this Ab at depleting blood basophils (FIG. 15) suggests that a mechanism other than FcεRI crosslinking and cell signaling (possibly ADCC or opsonization) is responsible for basophil elimination or redistribution.

Example 4. Prevention of Anaphylactic Response to a Second FcεRIα Epitope

Figure 16:
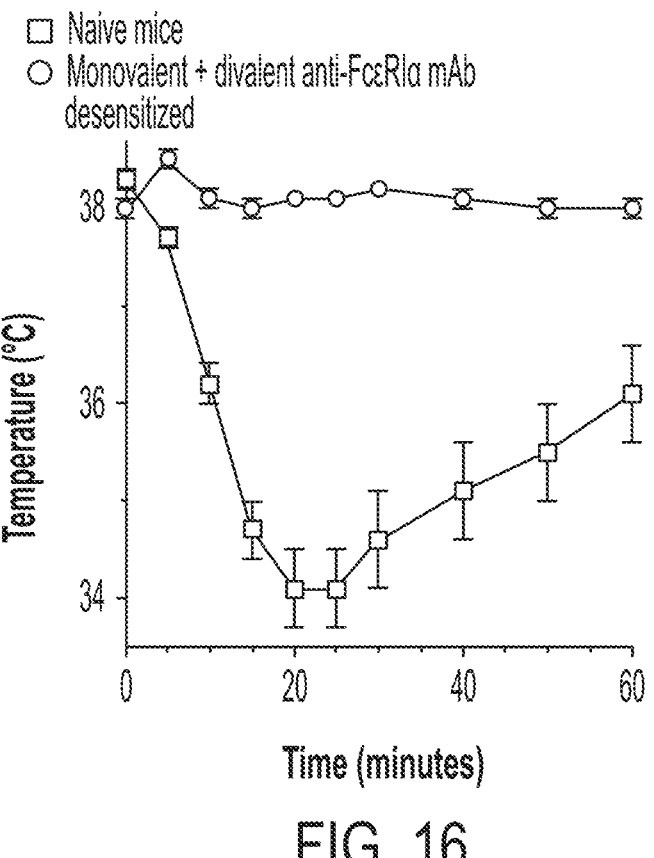
FIG. 16 shows that desensitization to one FcεRIα epitope prevents the anaphylactic response to a second FcεRIα epitope. HuFcεRIα mice (4/group) were desensitized by i.v. injection of 100 μg of mv huIgG1 IE7, followed the next day by i.v. injection of 100 μg of dv huIgG1 IE7. Neither injection caused a temperature drop. One day after the last IE7 injection, these IE7-treated mice and naive mice were injected i.v. with 100 μg of mAb IB10, which binds to an epitope of huFcεRIα that is not bound or blocked by IE7. Rectal temperatures were followed for the next 60 minutes. Means and SEMs are shown.

To determine whether desensitization to one FcεRIα epitope prevents an anaphylactic response to a second FcεRIα epitope, huFcεRIα mice (4/group) were desensitized by i.v. injection of 100 μg of mv huIgG1 IE7, followed the next day by i.v. injection of 100 μg of dv huIgG1 IE7. Neither injection caused a temperature drop. One day after the last IE7 injection, all mice were injected i.v. with 100 μg of mAb IB10, which binds to an epitope of huFcεRIα that is not bound or blocked by IE7. Hypothermia was not observed in desensitized mice (FIG. 16).

Example 5. Improved Safety of Monovalent Anti-FcεRIα Monoclonal Antibody

Figure 17:
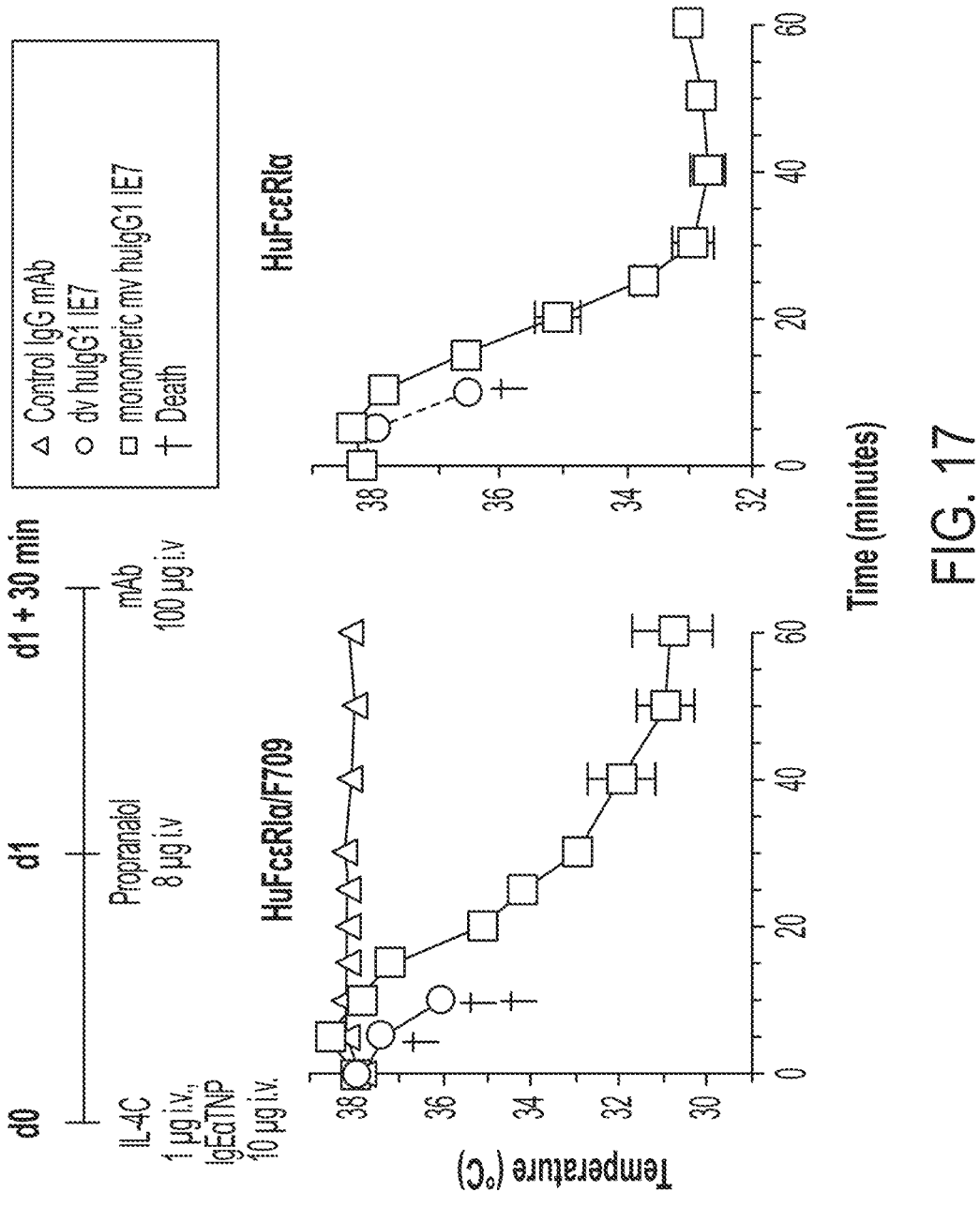
FIG. 17 shows that mv huIgG1 IE7 causes significantly less severe anaphylaxis than dv huIgG1 IE7 in IL-4C/propranolol-treated huFcεRIα/IL-4Ra$^{F709}$ mice (which, in addition to substitution of mouse FcεRIα with human FcεRIα, have a mutation in IL-4Ra that increases the response to IL-4 by blocking the inhibitory effects of IL-4) and huFcεRIα mice.

Investigators compared the safety of mv and dv anti-FcεRIα mAbs for single dose desensitization of mast cells and suppression of IgE-mediated allergy. Mice were treated with IL-4C (a long-acting form of IL-4) and the β-adrenergic receptor blocker propranolol to make them highly sensitive to development of anaphylaxis, then challenged with dv or mv huIgG1 IE7. Rectal temperatures were followed for 1 hour. Results indicate that desensitization with mv anti-FcεRIα mAb provides a safety advantage over desensitization with the dv form of the same mAb (FIG. 17).

Figure 18:
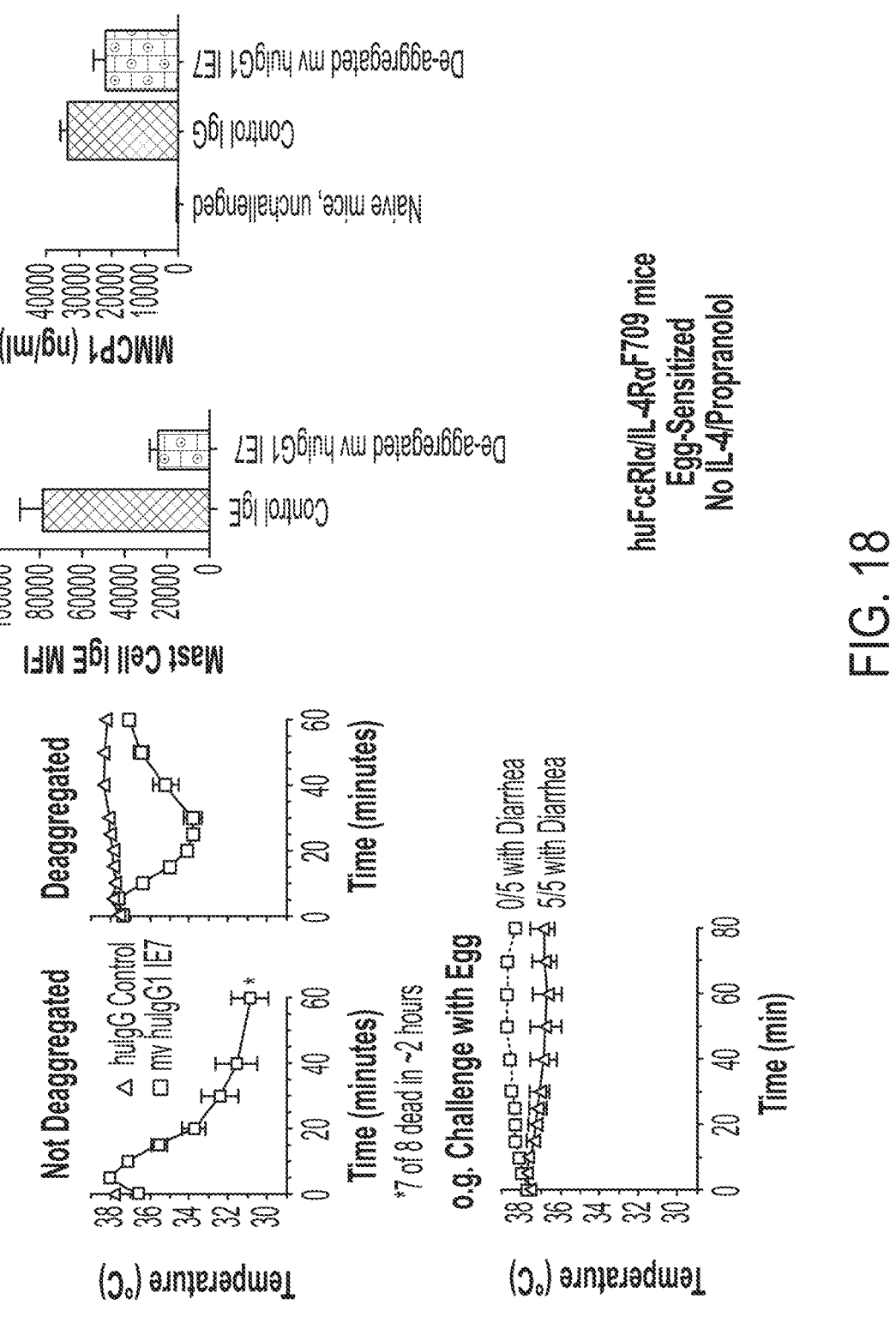
FIG. 18 shows that deaggregation reduces the ability of mv huIgG1 IE7 to induce anaphylaxis in egg-allergic huFcεRIα/IL-4Rα$^{F709}$ mice but does not prevent desensitization, as shown by inhibition of the hypothermia and diarrheal responses to challenge with egg by oral gavage.

Example 6. Deaggregation of MV Anti-FcεRIα mAb Limits Mast Cell Degranulation The effect of deaggregating the mv anti-FcεRIα mAbs used for desensitization was investigated. IL-4Rα$^{F709}$ mice have a mutation in their IL-4 receptor that increases their sensitivity to IL-4. When bred onto huFcεRIα mice, this mutation allows the induction of egg allergy. In this experiment, egg-allergic huFcεRIα/IL-4Rα$^{F709}$ mice were injected i.v. with 100 μg of non-deaggregated (~95% monomer, as determined by analytical ultracentrifugation) or gel filtration-deaggregated (>99.5% monomer) or control IgG mAb and followed for 1 hour for development of hypothermia. Mice injected with deaggregated mv huIgG1 IE7 were evaluated the next day for development of hypothermia and diarrhea following oral gavage (o.g.) with egg, and for mast cell degranulation (serum MMCP1 level) and loss of mast cell IgE during 4 hours after o.g. challenge with egg. Results are shown in FIG. 18.

Figure 19:
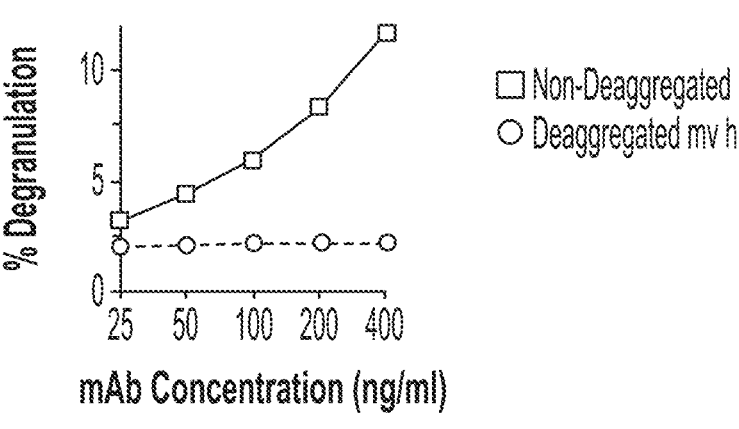
FIG. 19 shows that deaggregation of mv huIgG1 IE7 prevents its ability to induce LAD2 cell degranulation in vitro.

In another experiment, deaggregated or non-deaggregated mv huIgG1 IE7 was added to cultured cells of the LAD2 human mast cell line at concentrations ranging from 25 ng/mL to 400 ng/mL. The percent of mast cell degranulation was determined by hexosaminidase release (FIG. 19). This in vitro assay can be used to test batches of mv anti-FcεRIα mAb and to elucidate desensitization mechanisms.

Figure 20:
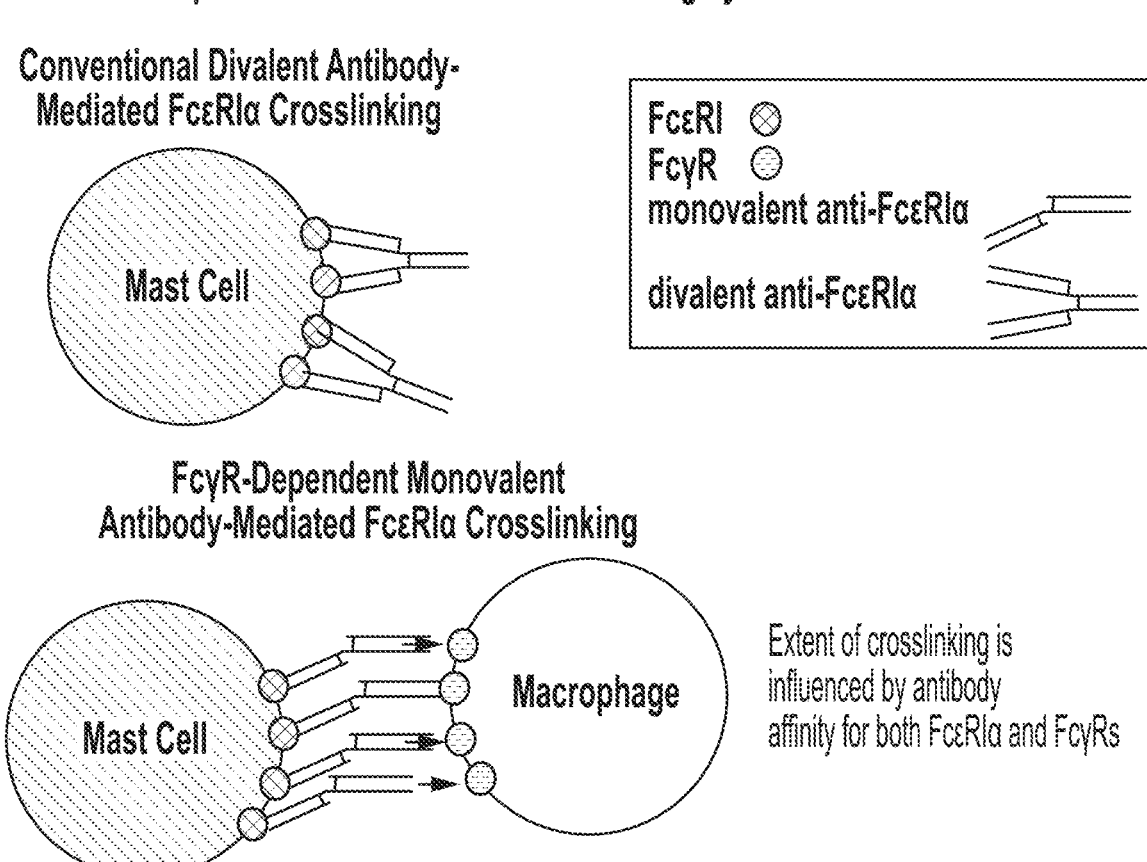
FIG. 20 shows a diagrammatic representation of how mv anti-FcεRIα mAb could crosslink FcεRT by simultaneously binding to FcεRT through its V region antigen binding site and to Fcγ receptors (FcγRs) on another cell through its Fc region.
Figures 21, 22:
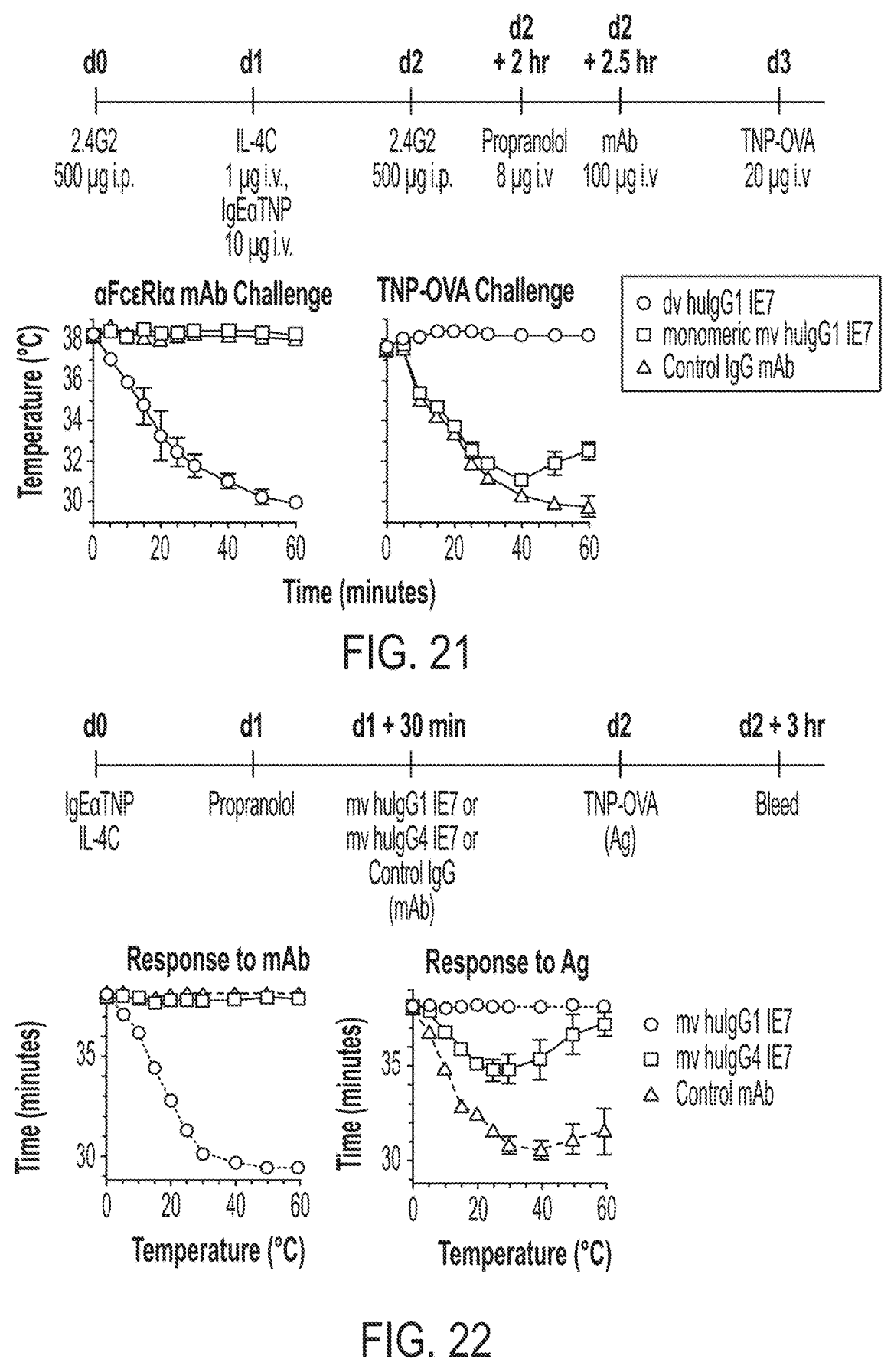

Example 7. Contribution of Avidity for Fcγ Receptors to Induction of Anaphylaxis and Suppression of IgE-Mediated Disease MV Anti-FcεRIα mAb Investigators explored whether mv anti-FcεRIα mAb can crosslink FcεRI by simultaneously binding through its V region antigen-binding site to FcεRI and through its Fc region to FcγRs on another cell (FIG. 20). HuFcεRIα mice were sensitized with IgE anti-TNP mAb, IL-4C, and propranolol, and were treated with the mAb 2.4G2, which blocks mouse FcγRs. Mice where then injected with dv huIgG1 IE7, deaggregated mv huIgG1 IE7, or a control IgG1 mAb, and followed for 1 hour for development of hypothermia. The next day, all mice were challenged i.v. with TNP-OVA and again followed for 1 hour for development of hypothermia. Data show that pre-treatment with anti-FcγR mAb prevented induction of hypothermia by mv, but not by dv huIgG1 IE7, but also blocked the ability of mv, but not dv huIgG1 IE7 to protect against IgE-mediated anaphylaxis (FIG. 21).

To determine whether investigators could optimize safety and efficacy of mv anti-FcεRIα mAbs by "tuning" mv IE7 avidity for FcγRs, huFcεRIα/IL-4Rα$^{F709}$ mice were sensitized with IgE anti-TNP mAb, IL-4C, and propranolol, injected with deaggregated mv huIgG1 IE7 or mv huIgG4 IE7, and challenged the next day i.v. with TNP-OVA. Mice were followed for development of hypothermia after injection of the mv mAb and after challenge with the antigen TNP-OVA. Results demonstrate that decreasing mv IE7 avidity for FcγRs by replacing huIgG1 with huIgG4 heavy chain constant regions prevents direct induction of anaphylaxis and reduces protection against IgE-mediated anaphylaxis (FIG. 22).

Figure 23:
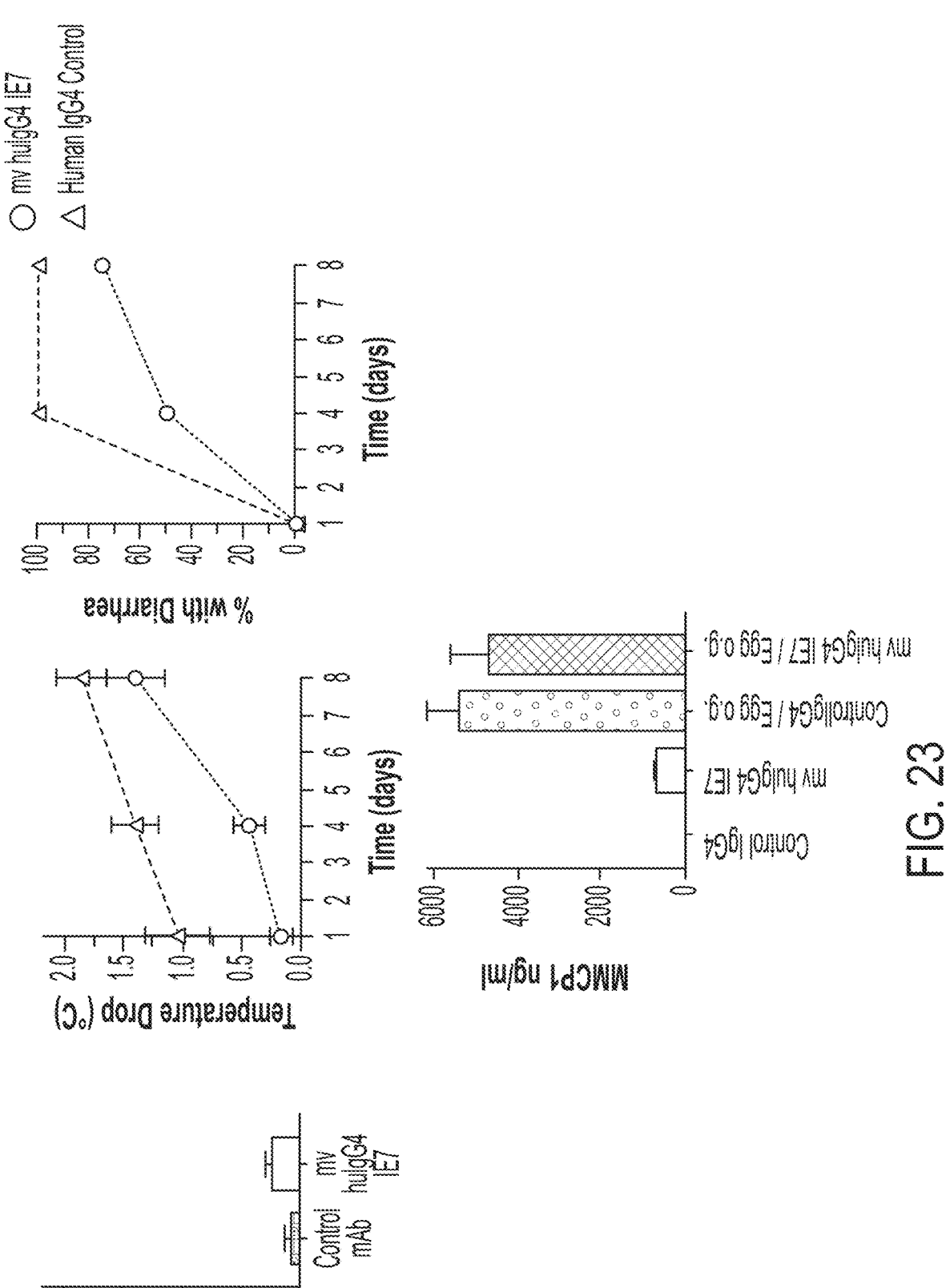
FIG. 23 shows that deaggregated mv huIgG4 IE7 desensitizes egg-allergic huFcεRIα/IL-4Rα$^{F709}$ mice without inducing anaphylaxis.

In another experiment, egg-allergic huFcεRIα/IL-4Rα$^{F709}$ mice were injected i.v. with 100 μg of deaggregated mv huIgG4 IE7 or isotype control mAb, then challenged o.g. with 100 mg of egg the next day and 3 and 7 days after that. Mice were evaluated for development of hypothermia after injection of mv huIgG4 IE7 and for hypothermia and diarrhea after each o.g. challenge. Mice were also evaluated for mast cell degranulation (serum MMCP1 level) 4 hours after the first o.g. challenge. The results demonstrate that mv huIgG4 IE7 can safely desensitize egg-allergic mice that are highly sensitive to the development of anaphylaxis (FIG. 23).

Figure 24:
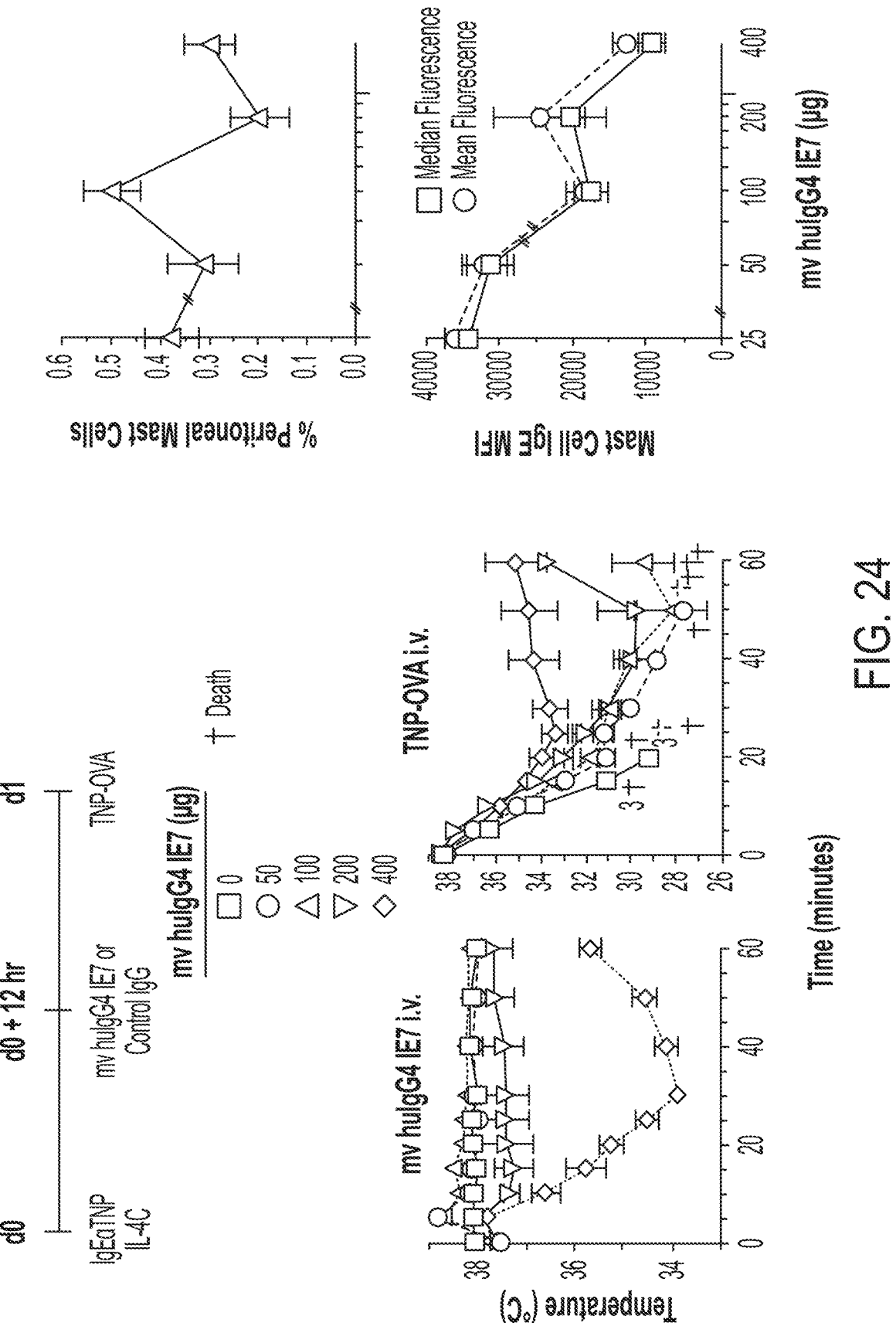
FIG. 24 shows dose-dependent effects of mv huIgG4 IE7 on mast cells and IgE-mediated anaphylaxis in IL-4C-treated huFcεRIα/IL-4Rα$^{F709}$ mice.

To study dose-dependent effects of mv huIgG4 IE7 on mast cells and IgE-mediated anaphylaxis, huFcεRIα/IL-4Rα$^{F709}$ mice were injected i.v. with IgE anti-TNP mAb and IL-4C. Twelve hours later, mice were injected i.v. with 0-400 μg of deaggregated mv huIgG4 IE7 and followed for 60 minutes for development of hypothermia. Twelve hours after that, mice were injected i.v. with TNP-OVA and followed for 60 minutes for development of hypothermia and survival. One hour after TNP-OVA injection, peritoneal mast cells were obtained and analyzed by flow cytometry for percent of mast cells among peritoneal wash-out cells and for surface IgE on these cells. Results are shown in FIG. 24.

In summary, consistent with the lower avidity of huIgG4 than huIgG1 for FcγRs, induction of anaphylaxis is decreased by administration of mv IE7 having huIgG4 heavy chain constant regions, compared with the huIgG1 form.

Figure 25:
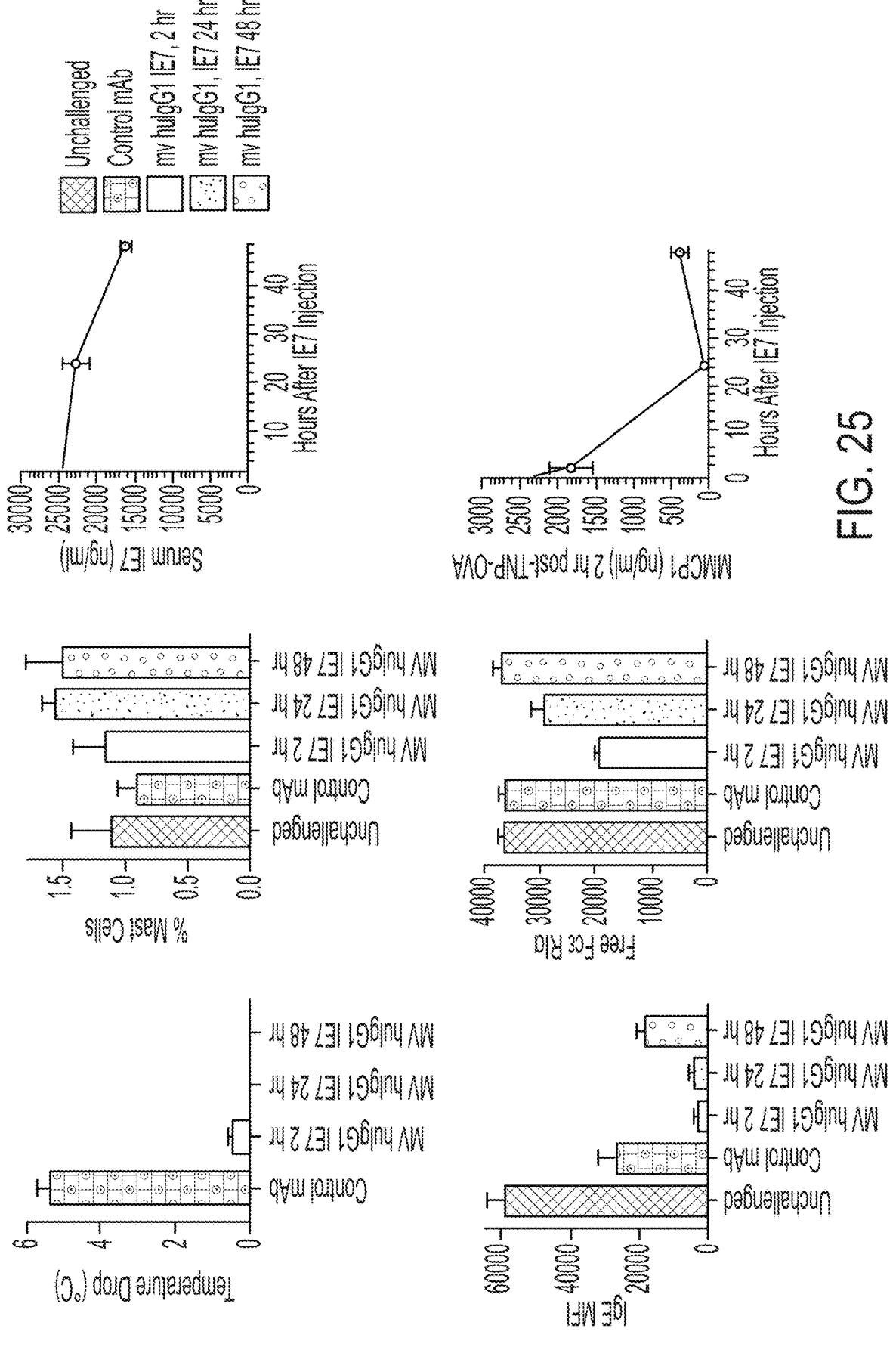
FIG. 25 shows that suppression of anaphylaxis by mv huIgG1 IE7 is seen in two hours and outlasts its suppression of mast cell IgE expression.

Example 8. Suppression of IgE-Mediated Anaphylaxis Is Not Entirely Due to Removal of IgE From Mast Cells To study the relationship between suppression of anaphylaxis and suppression of mast cell IgE expression by mv huIgG1 IE7, IgE anti-TNP mAb-sensitized huFcεRIα mice were given a single i.v. injection of 100 μg of mv huIgG1 IE7. Mice were followed for 48 hours for (i) hypothermia response to i.v. TNP-OVA, (ii) percent of mast cells among peritoneal lavage cells, (iii) serum levels of mv huIgG1 IE7, (iv) IgE on peritoneal mast cells, (v) mast cell FcεRI that was not occupied by IgE, and (vi) mast cell degranulation 2 hours post i.v. TNP-OVA challenge. Results show that a single dose of mv huIgG1 IE7 desensitizes mice for at least 48 hours; that this treatment has little effect on peritoneal mast cell number; that mv huIgG1 IE7 has a relatively long in vivo half-life; that desensitization persists despite the reacquisition of IgE by mast cells; that the loss of mast cell IgE exceeds the loss of mast cell FcεRI; and that mast cell degranulation over the 2 hours after challenge is less dramatic than the suppression of hypothermia (FIG. 25). These data suggest that induction of shock may be suppressed by a delay in mast cell degranulation, such that insufficient mediators are released at one time to cause shock, even when degranulation is not completely prevented.

Figure 26:
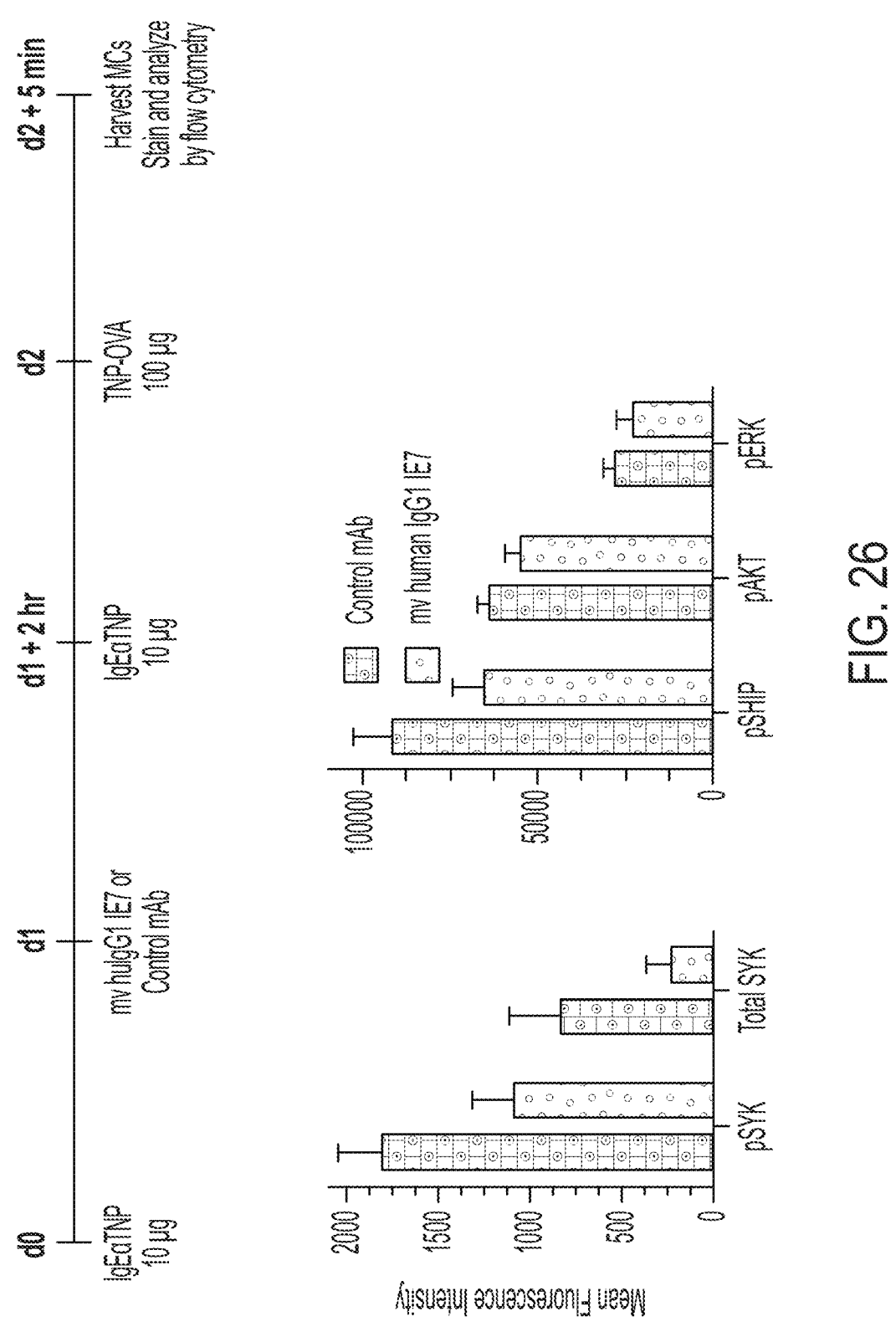
FIG. 26 shows in vivo suppression of FcεRI signaling by mv huIgG1 IE7.

Example 9. Desensitization Is Accompanied by Selective Loss of Some Mast Cell Signaling Molecules To determine the effect of mv huIgG1 IE7 on FcεRI signaling, huFcεRIα mice were sensitized with IgE anti-TNP mAb, treated with mv huIgG1 IE7 or control mAb, and challenged 1 day later i.p. with TNP-OVA. Peritoneal mast cells were obtained 5 minutes after challenge and stained for phospho-SYK, total SYK, phospho-SHIP, phospho-AKT, and phospho-ERK. Expression of these markers on mast cells (large, granular c-kit⁺ cells) was evaluated by flow cytometry. Mv huIgG1 IE7 reduced expression of SYK, phospho-SYK, and phospho-SHIP, but not of phospho-AKT or phospho-ERK. FIG. 26 shows the study design and results. Because SYK phosphorylation is required for mast cell degranulation, the loss of SYK and phospho-SYK likely contribute to mast cell desensitization by mv huIgG1 IE7.

The foregoing description of the specific embodiments will so fully reveal the general nature of the disclosed subject matter that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The disclosed subject matter is further described by the following claims.

---

The invention claimed is:

1. A monovalent monoclonal antibody (mAb) comprising one light chain, one heavy chain comprising SEO ID NO: 12, wherein the heavy chain comprises a variable region comprising SEQ ID NO: 4 and a constant region comprising an E356K mutation (corresponding to amino acid residue 378 of SEQ ID NO.12) and a D399K mutation (corresponding to amino acid residue 421 of SEQ ID NO:12), and one truncated heavy chain comprising SEO ID NO: 13, wherein the mAB specifically binds an epitope of FcεRIα, and wherein the mAb comprises complimentary determining regions having SEQ ID NO: 5, SEQ ID NO: 6, SEQ ID NO: 7; SEQ ID NO: 8; SEQ ID NO: 9; and SEQ ID NO: 10.

2. The monovalent mAb according to claim 1, wherein the mAb does not compete with IgE for binding to FcεRIα.

3. The monovalent mAb according to claim 1, wherein the epitope of FcεRIα is the same epitope bound by IE7.

4. The monovalent mAb according to claim 1, wherein the mAb binds to human FcεRIα.

5. The monovalent mAb according to claim 1, wherein the light chain is a kappa chain.

6. The monovalent mAb according to claim 1, wherein the heavy chain is a gamma chain.

7. The monovalent mAb according to claim 6, wherein the heavy chain is gamma subclass 4.

8. The monovalent mAb according to claim 1, wherein the light chain comprises a variable region encoded by SEQ ID NO: 1.

9. The monovalent mAb according to claim 1, wherein the heavy chain comprises a variable region encoded by SEQ ID NO: 2.

10. A pharmaceutical composition comprising the monovalent mAb according to claim 1.

11. A polynucleotide or a combination of polynucleotides encoding the monovalent mAb according to claim 1.

12. A vector comprising the polynucleotide or combination of polynucleotides according to claim 11.

13. A host cell comprising the polynucleotide or combination of polynucleotides according to claim 11.

* * * * *

SEQUENCE LISTING

<160> NUMBER OF SEQ ID NOS: 13

<210> SEQ ID NO 1
<211> LENGTH: 324
<212> TYPE: DNA
<213> ORGANISM: Homo sapiens

<400> SEQUENCE: 1

```
gatatcgtga tgacccaaac tccatcttcc atgtatgcat ctctaggaga gagagtcact       60
atcacttgca aggcgagtca ggacattaat aactatttaa gctggttcca gcagaaacca      120
gggagatctc ctaagaccct gatctatcgt gcaaacagat tgatggatgg ggtcccatca      180
aggatcagag gcagtggatc tgggcaagat tattctctca ccatcagcag cctggagtat      240
gaagatatgg gaatttatta ttgtctacta tataatgagt ttccgtggat gttcggtgga      300
ggcaccaagc tggaaatcaa acgg                                             324
```

<210> SEQ ID NO 2
<211> LENGTH: 351
<212> TYPE: DNA
<213> ORGANISM: Homo sapiens

<400> SEQUENCE: 2

```
caggtgcagc tgcaggagtc aggggggagac gtagtgaagc ctggagggtc cctgaaactc       60
tcctgtgcag cctctggatt cactttcagt ttctatggca tgtcttgggt tcgtcagact      120
ccagacaaga aactggagtg ggtcgcaacc attagtggtg gtggtaatta cacctactat      180
ccagacagtg tgaaggggcg attcaccatc tccagagaca atgccatgaa caccctttac      240
ctgcaaatga acagtctgaa gtctgaagac acagccatgt attattgtgt gagagcctac      300
tatggtaatt ggaattctta ctggggccaa gggactctgg tcactgtctc t              351
```

<210> SEQ ID NO 3
<211> LENGTH: 108
<212> TYPE: PRT
<213> ORGANISM: Homo sapiens

<400> SEQUENCE: 3

```
Asp Ile Val Met Thr Gln Thr Pro Ser Ser Met Tyr Ala Ser Leu Gly
1               5                   10                  15

Glu Arg Val Thr Ile Thr Cys Lys Ala Ser Gln Asp Ile Asn Asn Tyr
```

-continued

```
                  20                  25                  30

Leu Ser Trp Phe Gln Gln Lys Pro Gly Arg Ser Pro Lys Thr Leu Ile
        35                  40                  45

Tyr Arg Ala Asn Arg Leu Met Asp Gly Val Pro Ser Arg Ile Arg Gly
        50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Leu Tyr Asn Glu Phe Pro Trp
                85                  90                  95

Met Phe Gly Gly Gly Thr Lys Leu Glu Ile Lys Arg
            100                 105
```

```
<210> SEQ ID NO 4
<211> LENGTH: 117
<212> TYPE: PRT
<213> ORGANISM: Homo sapiens

<400> SEQUENCE: 4

Gln Val Gln Leu Gln Glu Ser Gly Gly Asp Val Val Lys Pro Gly Gly
1                   5                   10                  15

Ser Leu Lys Leu Ser Cys Ala Ala Ser Gly Phe Thr Phe Ser Phe Tyr
                20                  25                  30

Gly Met Ser Trp Val Arg Gln Thr Pro Asp Lys Lys Leu Glu Trp Val
        35                  40                  45

Ala Thr Ile Ser Gly Gly Gly Asn Tyr Thr Tyr Tyr Pro Asp Ser Val
        50                  55                  60

Lys Gly Arg Phe Thr Ile Ser Arg Asp Asn Ala Met Asn Thr Leu Tyr
65                  70                  75                  80

Leu Gln Met Asn Ser Leu Lys Ser Glu Asp Thr Ala Met Tyr Tyr Cys
                85                  90                  95

Val Arg Ala Tyr Tyr Gly Asn Trp Asn Ser Tyr Trp Gly Gln Gly Thr
                100                 105                 110

Leu Val Thr Val Ser
        115
```

```
<210> SEQ ID NO 5
<211> LENGTH: 6
<212> TYPE: PRT
<213> ORGANISM: Homo sapiens

<400> SEQUENCE: 5

Gln Asp Ile Asn Asn Tyr
1                   5
```

```
<210> SEQ ID NO 6
<211> LENGTH: 3
<212> TYPE: PRT
<213> ORGANISM: Homo sapiens

<400> SEQUENCE: 6

Arg Ala Asn
1
```

```
<210> SEQ ID NO 7
<211> LENGTH: 9
<212> TYPE: PRT
<213> ORGANISM: Homo sapiens

<400> SEQUENCE: 7
```

-continued

```
Leu Leu Tyr Asn Glu Phe Pro Trp Met
1               5

<210> SEQ ID NO 8
<211> LENGTH: 8
<212> TYPE: PRT
<213> ORGANISM: Homo sapiens

<400> SEQUENCE: 8

Gly Phe Thr Phe Ser Phe Tyr Gly
1               5

<210> SEQ ID NO 9
<211> LENGTH: 8
<212> TYPE: PRT
<213> ORGANISM: Homo sapiens

<400> SEQUENCE: 9

Ile Ser Gly Gly Gly Asn Tyr Thr
1               5

<210> SEQ ID NO 10
<211> LENGTH: 11
<212> TYPE: PRT
<213> ORGANISM: Homo sapiens

<400> SEQUENCE: 10

Val Arg Ala Tyr Tyr Gly Asn Trp Asn Ser Tyr
1               5                   10

<210> SEQ ID NO 11
<211> LENGTH: 234
<212> TYPE: PRT
<213> ORGANISM: Homo sapiens

<400> SEQUENCE: 11

Met Tyr Arg Met Gln Leu Leu Ser Cys Ile Ala Leu Ser Leu Ala Leu
1               5                   10                  15

Val Thr Asn Ser Asp Ile Val Met Thr Gln Thr Pro Ser Ser Met Tyr
                20                  25                  30

Ala Ser Leu Gly Glu Arg Val Thr Ile Thr Cys Lys Ala Ser Gln Asp
            35                  40                  45

Ile Asn Asn Tyr Leu Ser Trp Phe Gln Gln Lys Pro Gly Arg Ser Pro
        50                  55                  60

Lys Thr Leu Ile Tyr Arg Ala Asn Arg Leu Met Asp Gly Val Pro Ser
65                  70                  75                  80

Arg Ile Arg Gly Ser Gly Ser Gly Gln Asp Tyr Ser Leu Thr Ile Ser
                85                  90                  95

Ser Leu Glu Tyr Glu Asp Met Gly Ile Tyr Tyr Cys Leu Leu Tyr Asn
            100                 105                 110

Glu Phe Pro Trp Met Phe Gly Gly Gly Thr Lys Leu Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190
```

-continued

```
Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 12
<211> LENGTH: 469
<212> TYPE: PRT
<213> ORGANISM: Homo sapiens

<400> SEQUENCE: 12

Met Tyr Arg Met Gln Leu Leu Ser Cys Ile Ala Leu Ser Leu Ala Leu
1               5                   10                  15

Val Thr Asn Ser Ile Ser Gln Val Gln Leu Gln Glu Ser Gly Gly Asp
                20                  25                  30

Val Val Lys Pro Gly Gly Ser Leu Lys Leu Ser Cys Ala Ala Ser Gly
            35                  40                  45

Phe Thr Phe Ser Phe Tyr Gly Met Ser Trp Val Arg Gln Thr Pro Asp
        50                  55                  60

Lys Lys Leu Glu Trp Val Ala Thr Ile Ser Gly Gly Gly Asn Tyr Thr
65                  70                  75                  80

Tyr Tyr Pro Asp Ser Val Lys Gly Arg Phe Thr Ile Ser Arg Asp Asn
                85                  90                  95

Ala Met Asn Thr Leu Tyr Leu Gln Met Asn Ser Leu Lys Ser Glu Asp
            100                 105                 110

Thr Ala Met Tyr Tyr Cys Val Arg Ala Tyr Tyr Gly Asn Trp Asn Ser
        115                 120                 125

Tyr Trp Gly Gln Gly Thr Leu Val Thr Val Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
```

-continued

```
                325                     330                     335

Asn Gly Lys Glu Tyr Lys Cys Lys Val Ser Asn Lys Ala Leu Pro Ala
            340                     345                 350

Pro Ile Glu Lys Thr Ile Ser Lys Ala Lys Gly Gln Pro Arg Glu Pro
            355                     360                 365

Gln Val Tyr Thr Leu Pro Pro Ser Arg Glu Glu Met Thr Lys Asn Gln
    370                     375                 380

Val Ser Leu Thr Cys Leu Val Lys Gly Phe Tyr Pro Ser Asp Ile Ala
385                     390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
    450                 455                 460

Leu Ser Pro Gly Lys
465

<210> SEQ ID NO 13
<211> LENGTH: 247
<212> TYPE: PRT
<213> ORGANISM: Homo sapiens

<400> SEQUENCE: 13

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Asp
            180                 185                 190

Thr Thr Pro Pro Val Leu Asp Ser Asp Gly Ser Phe Phe Leu Tyr Ser
            195                 200                 205

Asp Leu Thr Val Asp Lys Ser Arg Trp Gln Gln Gly Asn Val Phe Ser
    210                 215                 220
```

-continued

```
Cys Ser Val Met His Glu Ala Leu His Asn His Tyr Thr Gln Lys Ser
225                 230                 235                 240

Leu Ser Leu Ser Pro Gly Lys
                245
```